United States Patent [19]

König et al.

[11] Patent Number: 5,011,825

[45] Date of Patent: Apr. 30, 1991

[54] PEPTIDES INFLUENCING DIURESIS AND NATRIURESIS, A PROCESS FOR THEIR PREPARATION, AGENTS CONTAINING THEM, AND THEIR USE

[75] Inventors: Wolfgang König, Hofheim am Taunus; Gerhard Breipohl; Rolf Geiger, both of Frankfurt am Main; Jochen Knolle, Kriftel; Max Hropot, Flörsheim am Main, all of Fed. Rep. of Germany

[73] Assignee: Hoechst Aktiengesellschaft, Frankfurt am Main, Fed. Rep. of Germany

[21] Appl. No.: 463,782

[22] Filed: Jan. 8, 1990

Related U.S. Application Data

[63] Continuation of Ser. No. 59,842, Jun. 9, 1987, abandoned.

[30] Foreign Application Priority Data

Jun. 11, 1986 [DE] Fed. Rep. of Germany ....... 3619633

[51] Int. Cl.$^5$ .................... C07K 7/06; A61K 37/64
[52] U.S. Cl. .................................. 514/18; 514/17; 530/317; 530/329; 530/330; 530/331
[58] Field of Search .................. 530/329–331, 530/317; 514/17, 18

[56] References Cited

U.S. PATENT DOCUMENTS

| 4,389,342 | 6/1983 | Reinhard | 530/329 |
| 4,518,527 | 5/1985 | Numa et al. | 514/17 |
| 4,579,840 | 4/1986 | Hahn | 530/330 |
| 4,686,282 | 8/1987 | Hahn | 530/329 |
| 4,692,511 | 9/1987 | Hahn | 530/329 |
| 4,751,284 | 6/1988 | Forssmann . | |
| 4,782,044 | 11/1988 | Forssman . | |

FOREIGN PATENT DOCUMENTS

| 140731 | 5/1985 | European Pat. Off. . | |
| 146266 | 6/1985 | European Pat. Off. . | |
| 166612 | 1/1986 | European Pat. Off. . | |
| 59-130254 | 7/1984 | Japan . | |
| 60-78996 | 5/1985 | Japan | 514/17 |
| WO85/02850 | 7/1985 | World Int. Prop. O. . | |

OTHER PUBLICATIONS

Chem. Abstr., vol. 81, (1974), 50025.
Chem. Abstr., vol. 77, (1972), 20028.

*Primary Examiner*—Lester L. Lee
*Attorney, Agent, or Firm*—Finnegan, Henderson, Farabow, Garrett and Dunner

[57] ABSTRACT

The invention relates to peptides of the formula

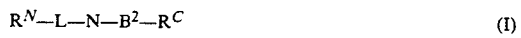

in which $R^N$ denotes an acyl radical, L denotes a radical of a lipophilic, neutral α-amino acid, N denotes a radical of an neutral α-amino acid, $B^2$ denotes the radical of a basic α-amino acid, and $R^C$ denotes an amido radical; a process for their preparation, agents containing these peptides, and their use.

13 Claims, No Drawings

PEPTIDES INFLUENCING DIURESIS AND NATRIURESIS, A PROCESS FOR THEIR PREPARATION, AGENTS CONTAINING THEM, AND THEIR USE

This application is a continuation of application Ser. No. 059,842 filed June 9, 1987.

The invention relates to new peptides of the formula I, $$R^N-L-N'B^2-R^C \qquad (I)$$

in which $R^N$ represents a radical of the formula II;

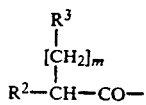

$R^2$ represents hydrogen or a radical of the formula $R-[A]_n-NH-$;

$R^3$ denotes amino, guanidino, $(C_1-C_3)$-alkylamino or $di(C_1-C_3)$-alkylamino;

m denotes an integer from 1 to 6;

A represents a radical of the formula $-NH-CR^4R^5-CO-$;

R denotes hydrogen, $(C_1-C_6)$-alkanoyl, $(C_7-C_{11})$-aroyl, in which the aromatic moiety is optionally mono- or disubstituted by $(C_1-C_4)$-alkyl, $(C_1-C_4)$-alkoxy, $(C_1-C_4)$alkylthio, halogen, carbamoyl, $(C_1-C_4)$-alkoxycarbonyl and/or sulfamoyl, or is monosubstituted by methylenedioxy, or denotes $(C_5-C_7)$-cyclo-alkyl-$(C_1-C_3)$-alkanoyl or $(C_6-C_{14})$-aryl-$(C_1-C_3)$-alkanoyl, where a $-CH_2-$ group in the radicals R # hydrogen is optionally replaced by $-O-$ or $-S-$;

n is 0 or 1;

$R^4$ and $R^5$ are identical or different and denote hydrogen, $(C_1-C_6)$-alkyl or $(C_7-C_{11})$-aralkanoyl;

L represents the radical of a lipophilic neutral α-amino acid, and preferably represents Pro, D-Pro or a radical of the formula $-NH-CH(R^6)-CO-$;

$R^6$ denotes $(C_1-C_6)$-alkyl which is optionally monodenotes substituted by hydroxyl, $(C_1-C_6)$-alkoxy, $(C_1-C_6)$-alkoxycarbonyl, carbamoyl or $R-NH$, R being as defined above but cannot be hydrogen, or denotes $(C_7-C_{11})$-aralkyl which is optionally monosubstituted on the aromatic ring by $(C_1-C_6)$-alkoxy, or denotes 3-indolylmethyl;

N represents the radical of a neutral α-amino acid, and preferably represents Pro, D-Pro or a radical of the formula $-NH-CH(R^7)-CO-$;

$R^7$ $(C_1-C_6)$-alkyl which is optionally monodenotes substituted by hydroxyl, $(C_1-C_6)$-alkoxy, $(C_1-C_6)$-alkoxycarbonyl, carbamoyl or $R-NH$, R being as defined above but cannot be hydrogen, or denotes $(C_7-C_{11})$-aralkyl which is optionally monosubstituted on the aromatic ring by $(C_1-C_6)$-alkoxy, or denotes 3-indolylmethyl;

$B^2$ represents the radical of a basic u-amino acid, and preferably represents a radical of the formula III

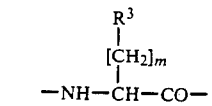

in which $R^3$ and m are as defined above;

$R^C$ represents a radical of the formula $-NR^9-CH(R^8)-(CO)_p-R^1$;

$R^8$ denotes a lipophilic side-chain which is preferably defined as $R^7$, with CH, CH2 or CH3 radicals which are present in the β-position with respect to $-NH-$ optionally being monohydroxylated, and $R^9$ denotes hydrogen; or $R^8$ and $R^9$ together denote $-[CH_2]_3-$ or $-[CH_2]_4-$;

p is 0 or 1;

$R^1$ represents hydrogen, hydroxyl or $(C_1-C_6)$-alkoxy in the case of $p = 0$;

$R^1$ represents $OR^{10}$ or $NR^{10}R^{11}$ in the case of $p = 1$; and $R^{10}$ and $R^{11}$ are identical or different and denote hydrogen, $(C_1-C_6)$-alkyl or $(C_7-C_{11})$-aralkyl; or $NR^{10}R^{11}$ represents pyrrolidino, piperidino or morpholino; or p is 1, R and $R^1$ together denote a bond, and the other radicals are as defined above, and to their physiologically tolerated salts.

Suitable salts are, in particular, salts with inorganic or organic acids such as, for example, HCl, HBr, $H_2SO_4$, $H_3PO_4$, maleic acid, fumaric acid, citric acid, tartaric acid and acetic acid. The chirality centers in the new peptides can each have the R, S or R,S configuration.

Alkyl can be straight-chain or branched. A corresponding statement applies to radicals derived therefrom, such as, for example alkoxy, alkylthio, alkylamino, dialkylamino, alkanoyl and aralkyl.

Cycloalkyl is to be understood to include alkyl-substituted radicals such as, for example, 4-methylcyclohexyl or 2,3-dimethylcyclopentyl.

$(C_6-C_{14})$-aryl is, for example, phenyl, naphthyl, biphenylyl or fluorenyl; phenyl is preferred. A corresponding statement applies to radicals derived therefrom, such as, for example, aryloxy, aroyl, aralkyl and aralkyloxy. Preferred aralkyl radicals are benzyl and phenethyl. Halogen denotes fluorine, chlorine, bromine or iodine, preferably chlorine or bromine.

The preferred radicals $R^N$, L, N, $B^2$ and $R^C$ are those which are derived from naturally occurring amino acids (see, for example, Schröder, Lübke, The Peptides, Volume I, New York 1965, pages 137-270), their antipodes or their simple metabolites.

The compounds of the formula I which are preferred are those in which

L represents the radical of isoleucine, valine, threonine, serine, $O-(C_1-C_9)$-alkylthreonine, $O-(C_1-C_9)$-alkyl serine, leucine, proline or of the ω-$(C_1-C_6)$-alkyl ester preferably tert. butyl ester of glutamic acid or aspartic acid;

N represents the radical of valine, isoleucine, leucine, phenylalanine, tryptophan, tyrosine which is optionally $O-(C_1-C_6)$-alkylated, glutamine, asparagine, γ-$(C_1-C_6)$alkyl glutamate or β-$(C_1-C_6)$-alkyl aspartate or ε-acyl-lysine, and $B^2$ denotes Arg, D-Arg, Lys or D-Lys.

The new peptides are either open-chain or cyclic with a linkage in the form of a peptide bond (R, $R^1$ = peptide bond).

The invention also relates to a process for the preparation of compounds of the formula I, which comprises coupling a fragment with a terminal carboxyl group, or its reactive derivative, with an appropriate fragment with a free amino group, where appropriate eliminating (a) protective group(s) temporarily introduced to protect other functional groups, and converting, where appropriate, the compound which has thus been obtained into its physiologically tolerated salt.

Fragments of a compound of the formula I with a terminal carboxyl group have the formulae IVa-IVf which follow R—OH (IVa)
R—A—OH (IVb)
$R^N$—OH (IVc)
$R^N$—L—OH (IVd)
$R^N$—L—N—OH (IVe)
$R^N$—L—N—$B^2$—OH (IVf)

Fragments of a compound of the formula I with a terminal amino group have the formulae Va-Vf which follow

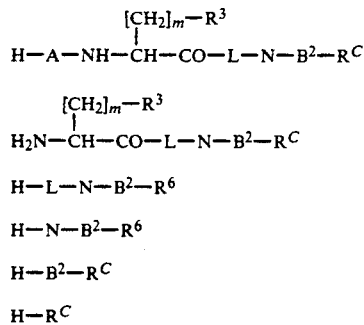

H—L—N—$B^2$—$R^6$ (Vc)

H—N—$B^2$—$R^6$ (Vd)

H—$B^2$—$R^C$ (Ve)

H—$R^C$ (Vf)

The synthesis of the compounds according to the invention follows the known methods of peptide chemistry as are described in detail, for example, in Houben-Weyl, Methoden der Organischen Chemie (Methods of Organic Chemistry), Volume 15 (Stuttgart, Thieme, 1974). The peptides are preferably prepared stepwise starting with the C-terminal amino acid, or by fragment-coupling (2 fragment +3 fragment or 3 fragment +2 fragment). Care must be taken in the fragment-coupling that the coupling methods used result in as Little racemization as possible. In the examples in this specification the fragment-coupling was principally effected by the DCC/HOObt method which, according to experience to date, provides the least racemization during the peptide synthesis. Also suitable are the active ester method with N-hydroxysuccinimide as ester component, coupling by use of propanephosphonic anhydride, and the mixed anhydride method using pivaloyl chloride.

Cyclopeptides of the formula I can be prepared, for example, by the procedure described in European Patent A2-135,722.

The results of in vivo tests, which are given hereinafter, show that the compounds according to the invention lastingly influence diuresis, natriuresis and kaliuresis.

A. Diuretic, natriuretic and kaliuretic action of the peptides according to the invention in Experimental Design 1 (dose 1 mg/kg rat, collection period: 90 min.)

|  | Urine (ml. $kg^{-1}$) | $Na^+$ ($\mu$mol. $kg^{-1}$) | $K^+$ ($\mu$mol. $kg^{-1}$) |
| --- | --- | --- | --- |
| Control | 1.267 | 65.2 | 29.5 |
| H-Arg-Ile-Asp(OtBu)-Arg-Ile-OH | 2.49 | 249.1 | 25.9 |
| Phenoxyacetyl-Arg-Ile-Asp(OtBu)-Arg-Ile-OH | 0.66 | 117.7 | 31.7 |
| H-Arg-Ile-Asp(OtBu)-Arg-Ile-ol | 1.56 | 155.4 | 59.4 |
| H-Arg-Ile-Asp(OtBu)-Arg-Leu-ol | 1.55 | 180.8 | 64.2 |
| H-Arg-Ile-Asp(OtBu)-Arg-Val-$NH_2$ | 1.95 | 184.7 | 89.2 |
| H-Arg-Ile-Asp(OtBu)-Arg-iso-butylamide | 1.43 | 131.6 | 51.3 |
| H-Arg-Ile-Asp(OtBu)-Arg-Trp-$NH_2$ | 1.97 | 225.0 | 33.0 |
| H-Arg-Ile-Asp(OtBu)-Arg-Ile-$NH_2$ | 1.34 | 159.8 | 35.4 |
| Z-Arg-Ile-Asp(OtBu)-Arg-Ile-ol (1 $\mu$g/kg) | 0.79 | 118.4 | 27.8 |
| Z-Arg-Ile-Asp(OtBu)-Arg-Ile-$NH_2$ | 1.51 | 263.2 | 63.3 |
| H-Arg-Pro-Val-Lys-Val-OH | 0.91 | 155.7 | 28.2 |
| H-Arg-Ile-Ser(tBu)-Arg-Ile-OH | 1.19 | 74.5 | 28.4 |
| H-Arg-Ile-D-Ser(tBu)-Arg-Ile-OH | 0.95 | 87.0 | 44.3 |
| H-Arg-Ile-Leu-Arg-Ile-OH | 2.03 | 149.8 | 50.1 |
| H-Arg-Ile-Phe-Arg-Ile-OH | 2.00 | 211.0 | 68.3 |
| H-Arg-Ile-Trp-Arg-Ile-OH | 0.67 | 112.8 | 57.5 |
| Z-Arg-Ile-Trp-Arg-Ile-OH | 1.64 | 208.6 | 37.1 |
| Z-Arg-Ile-Trp-Arg-Ile-OMe | 1.16 | 152.5 | 46.2 |
| cyclo-(Gly-Arg-Ile-Phe-Arg-Ile) | 1.58 | 196.2 | 57.7 |
| H-Arg-Val-Tyr(tBu)-Arg-Pro-OtBu | 0.28 | 59.2 | 21.9 |

Experimental Design 1: The rats were anesthetized with 0.1 ml of 10% strength thiobutabarbital sodium/100 g of body weight i.p. They received an NaCl infusion from 60 min before administration of the substance and continuing during the experiment (2.5 ml of a 0.9% strength NaCl solution $.h^{-1}.0.1$ $kg^{-1}$ body weight). The test substance was administered as an i.v. bolus in 0.5 ml of a 0.9% strength solution/100 g of body weight.

B. Diuretic, natruiuretic and kaliuretic action of the peptides according to the invention in Experimental Design 2 (dose: 1 mg/kg rat, colection period: 120 min.)

|  | Urine (ml. $kg^{-1}$) | $Na^+$ ($\mu$mol. $kg^{-1}$) | $K^+$ ($\mu$mol. $kg^{-1}$) |
| --- | --- | --- | --- |
| Control: | 0.520 | 31.5 | 25.8 |
| Z-Arg-Ile-Leu-D-Arg-Ile-OBzl | 0.52 | 66.9 | 36.2 |
| Z-D-Arg-Ile-Leu-Arg-Ile-OBzl | 0.59 | 86.3 | 38.1 |
| Z-Arg-Ile-D-Leu-Arg-D-Val-OBzl | 0.48 | 79.0 | 43.8 |
| Z-Arg-Ile-Leu-Arg-D-Val-OBzl | 0.43 | 88.6 | 36.7 |
| H-D-Arg-Ile-D-Leu-Arg-Ile-OH | 1.13 | 115.9 | 49.7 |
| H-Arg-Ile-Glu(OtBu)-Arg-Ile-$NH_2$ | 1.04 | 95.6 | 67.3 |
| $\epsilon$-Amino-hexanoyl-Ile-Asp(OtBu)-Arg-Ile-$NH_2$ | 0.82 | 54.9 | 38.0 |
| Z-Arg-Ile-Glu(OtBu)-Arg-Ile-$NH_2$ | 0.47 | 91.5 | 36.1 |
| Z-D-Arg-Ile-Leu-D-Arg-Ile-OBzl | 0.29 | 48.4 | 30.1 |
| Z-D-Arg-Ile-D-Leu-Arg-Ile-OBzl | 0.19 | 37.3 | 20.4 |
| Z-Arg-D-Val-Leu-Arg-D-Val-OBzl | 0.27 | 55.1 | 38.3 |
| H-Arg-Leu-Gln-Arg-Leu-OH | 0.25 | 30.2 | 23.7 |
| H-Lys-Ile-Asp(OtBu)-Arg-Ile-$NH_2$ | 0.08 | 10.6 | 22.1 |
| H-Arg-D-Val-Leu-Arg-Ile-OH | 0.57 | 83.77 | 34.9 |
| H-D-Arg-D-allo-Ile-D-Leu-Arg-Ile-OH | 0.87 | 95.1 | 35.5 |
| H-Arg-Ile-Leu-D-Arg-Ile-OH | 0.78 | 93.7 | 40.8 |
| H-D-Arg-Ile-Leu-D-Arg-Ile-OH | 0.28 | 61.4 | 33.9 |
| H-D-Arg-Ile-Leu-Arg-Ile-OH | 0.22 | 55.3 | 33.6 |
| H-Arg-Ile-Leu-Arg-D-Val-OH | 0.56 | 68.8 | 38.9 |
| cyclo-(Gly-Arg-Ile-Leu-Arg-Ile) (with 0.5 mg/kg) | 0.69 | 65.5 | 26.6 |
| H-Arg-Ile-D-Leu-Arg-D-Val-OH | 0.31 | 68.4 | 32.8 |
| Z-Arg-Ile-Ser(tBu)-Arg-Pro-OtBu | 0.44 | 88.9 | 37.8 |
| H-Arg-Ile-Ser(tBu)-Arg-Pro-OtBu | 0.63 | 136.8 | 31.5 |
| H-Arg-Trp-Asp(OtBu)-Arg-Phe-$NH_2$ | 0.66 | 148.7 | 37.1 |

| | Urine (ml. kg$^{-1}$) | Na$^+$ ($\mu$mol. kg$^{-1}$) | K$^+$ ($\mu$mol. kg$^{-1}$) |
| --- | --- | --- | --- |
| Fmoc-Arg-Pro-Cys(StBu)-Arg-Phe-OtBu | 0.65 | 143.0 | 16.5 |
| H-Arg-Pro-Cys(StBu)-Arg-Phe-OtBu | 0.32 | 87.5 | 11.1 |
| H-Lys-Phe-Leu-Lys-Phe-OH | 0.52 | 80.2 | 31.0 |
| H-Lys-Phe-Leu-Lys-Phe-NH$_2$ | 0.25 | 36.8 | 16.7 |
| cyclo-(D-Arg-Ile-D-Leu-Arg-Ile) (with 1 $\mu$g/kg) | 1.05 | 128.2 | 36.6 |

Experimental Design 2: The rats were anesthetized with 0.1 ml of 10% strength thiobutabarbital sodium/100 g of body weight i.p. They received an NaCl infusion from 60 min before administration of the substance up to administration of the substance (2.5 ml of a 0.85% strength NaCl solution .h$^{-1}$.0.1 kg$^{-1}$ body weight). After administration of the substance, the infusion rate was halved for one hour (1.25 ml.h$^{-1}$.0.1 kg$^{-1}$). Thereafter the infusion rate was again halved up to the end of the experiment (0.625 ml.h$^{-1}$.0.1 kg$^{-1}$). The test substance was administered as i.v. bolus in 0.1 ml of a 0.85% strength NaCl solution/100 g of body weight.

It is evident from the data that the peptides according to the invention can act both as diuretics and as natriuretics. However, in many examples only natriuresis is found, and this is sometimes even associated with antidiuresis. Since the potassium excretion does not exceed the control in some cases, it is possible from this class of substances to develop potassium-retaining natriuretics (for example H-Arg-Pro-Val-Lys-Val-OH), antidiuretics with a natriuretic action (for example Z-Arg-Ile-Asp(OtBu)Arg-Ile-ol) or medicaments with a diuretic and natriuretic action (for example H-Arg-Ile-Asp(OtBu)-Arg-Ile-OH or cyclo-(D-Arg-Ile-D-Leu-Arg-Ile). However, antidiuretics with an antinatriuretic action (for example H-Arg-Pro-Cys(StBu)-Arg-Phe-OtBu) were also found in this class of substances (for example H-Lys-Ile-Asp(OtBu)-Arg-Ile-NH$_2$).

Thus the invention also relates to the use of peptides of the formula I as medicaments which have a regulatory action on diuresis, natriuresis or kaliuresis and which can be used for disturbances of the water and electrolyte balance, to pharmaceutical agents containing these peptides, and to processes for the preparation of the agents, which comprise converting the peptides, together with a vehicle and, where appropriate, other additives and auxiliaries, into a suitable form for administration.

The peptides having a natriuretic and diuretic action can be used as medicaments for hypertension and dropsy. It would be possible to use the compounds which have a specific natriuretic action in elderly hypertensive patients in whom dehydration is to be avoided. The peptides having an antidiuretic action are appropriate in cases of polyuria or diabetes insipidus.

The peptides can be administered parenterally (i.v., s.c. or i.m.), singly or in combination, in a physiologically tolerated medium. The dose to be administered is, as a rule, 1 $\mu$g–5 mg/kg.

For parenteral administration, the active compounds or their physiologically tolerated salts are converted into solution, suspensions or emulsions, if desired with the substances customary for this purpose, such as solubilizers, emulsifiers or other auxiliaries. Examples of suitable solvents for the new active compounds and the corresponding physiologically tolerated salts are: water, physiological saline solutions or alcohols, for example ethanol, propanediol or glycerol, as well as sugar solutions such as glucose or mannitol solutions, or a mixture of the various solvents mentioned.

It is likewise possible to administer the active compounds by implants, for example composed of polylactide, polyglycolide, copolymers of lactic and glycolic acid or poly-3-hydroxybutyric acid, or intranasal formulations. On intranasal administration, the dose must be multiplied by ten because of the poorer absorption. The addition of a chelate-forming agent such as, for example, EDTA may have an advantageous effect on absorption. In addition, it is possible to administer the peptides in the form of their physiologically tolerated salts or metal complexes.

EXAMPLE 1

H-Arg-Ile-Asp(OtBu)-Arg-Ile-OH (a) Z-Arg(Z$_2$)-Ile-Obzl 1.3 ml of N-ethylmorpholine and 2.2 g of DCC are added, at 0° C., to a solution of 5.76 g of Z-Arg(Z2)—OH, 3.93 g of H-Ile-OBzl tosylate and 1.35 g of HOBt in 50 ml of dimethylformamide. The mixture is stirred at 0° C. for one hour and at room temperature for one hour. It is left to stand at room temperature overnight. The precipitate is filtered off with suction and discarded. The filtrate is concentrated in vacuo, and the residue is partitioned between ethyl acetate and water. The ethyl acetate phase is washed successively with saturated aqueous NaHCO$_3$ solution, with a KHSO$_4$/K2SO$_4$ buffer and with water. The solution is dried over Na$_2$SO$_4$ and concentrated. The residue is triturated with ether, filtered off with suction and dried.

Yield: 7.45 g, melting point 142°–144° C., $[\alpha]_D^{22} = -5.5°$ (c=1 in 90% acetic acid).

(b) H-Arg-Ile-OH acetate

Pd/carbon catalyst is added to a suspension of 7.3 g of Z-Arg(Z$_2$)-Ile-OBzl in 220 ml of 90% acetic acid, and hydrogen is passed through the solution. After the reaction is complete, the catalyst is filtered off with suction, and the filtrate is concentrated. The residue is triturated with ether and filtered off with suction.

Yield: 3.86 g, melting point 197°–200° C., $[\alpha]_D^{22} = +19.9°$ (c=1, 90% acetic acid).

(c) H-Asp(OtBu)-Arg-Ile-OH acetate 1.35 g of HOBt and 4.2 g of Z-Asp(OtBu)-ONSu are added to a suspension of 3.45 g of H-Arg-Ile-OH acetate in 50 ml of dimethylformamide. The mixture is left to stir at room temperature for one day, and is concentrated. The residue is subjected to countercurrent partition between 100 ml of half-saturated aqueous NaHCO$_3$ solution and 100 ml of ethyl acetate (5 stages). The fractions which contain pure Z-Asp(OtBu)-Arg-Ile-OH are concentrated, and the residue is dissolved in 70 ml of 90% acetic acid and catalytically hydrogenated as in Example 1b.

Yield: 2.22 g amorphous, $[\alpha]_D^{22} = +0.8°$ (c=1 in 90% acetic acid).

(d) Z-Ile-Asp(OtBu)-Arg-Ile-OH 2.22 g of HOBt and 6.6 g of Z-Ile-ONSu are added, at room temperature, to a suspension of 8.55 g of H-Asp(OtBu)-Arg-Ile-OH acetate in 80 ml of dimethylformamide. The mixture is stirred at room temperature for 5 hours, and is concentrated in vacuo. The residue is subjected to countercurrent partition between half-saturated aqueous NaHCO$_3$ solution and ethyl acetate (5 stages). The fractions which contain pure Z-Ile- Asp(OtBu)-Arg-Ile-OH are concentrated, and the residue is triturated with ether.

Yield: 10.7 g, melting point 177°-179° C., $[\alpha]_D^{22} = -30.2°$ (c=1 in 90% acetic acid).

(e) H-Ile-Asp(OtBu)-Arg-Ile-OH acetate 10.7 g of Z-Ile-Asp(OtBu)-Arg-Ile-OH are catalytically hydrogenated in 150 ml of 90% acetic acid in analogy to Example 1b.

Yield: 10.4 g, melting point 107°-117° C., $[\alpha]_D^{22} = -3.5°$ (c=1 in 90% acetic acid).

(f) Z-Arg(Z$_2$)-Ile-Asp(OtBu)-Arg-Ile-OH 13.6 g of Z-Arg(Z$_2$)-OTcp are added to a solution of 11.4 g of H-Ile-Asp(OtBu)-Arg-Ile-OH acetate and 2.45 g of HOBt in 180 ml of dimethylformamide. The mixture is left to react at room temperature for 24 hours, and is concentrated. The residue is triturated with ethyl acetate, filtered off with suction and dried. The substance is then triturated with saturated aqueous NaHCO$_3$ solution, filtered off with suction, washed with water and dried over P$_2$O$_5$.

Yield: 5.75 g, melting point 184°-186° C. $[\alpha]_D^{22} = -22.5°$ (c=1 in 90% acetic acid).

(g) H-Arg-Ile-Asp(OtBu)-Arg-Ile-OH diacetate 6.34 g of Z-Arg(Z$_2$)-Ile-Asp(OtBu)-Arg-Ile-OH are catalytically hydrogenated in 120 ml of 90% acetic acid in analogy to Example 1b.

Yield: 5.66 g

For purification, the substance is subjected to countercurrent partition between 100 ml of n-butanol and 100 ml of 10% acetic acid (7 stages).

Yield: 4.45 g, amorphous, $[\alpha]_D^{22} = -32.4°$ (c=1 in water).

EXAMPLE 2

H-Arg-Ile-Asp(OtBu)-Arg-Ile-ol (a) L-Isoleucinol.HOObt (=H-Ile-ol.HOObt)

11.4 g of LiAlH$_4$ are added to 250 ml of tetrahydrofuran which is cooled to −5° C. and stirred. 28.86 g (0.22 mole) of L-Isoleucine are added within 45 minutes to this stirred suspension. The mixture is then boiled under reflux for 4 hours. It is then cooled to 0° C., 250 ml of diethyl ether are added and, while stirring, 50 ml of water are slowly added dropwise. The precipitate is filtered off with suction, and the residue is extracted by boiling twice with 150 ml of methanol each time and filtered hot with suction. The combined filtrates are concentrated. The residue is taken up in 100 ml of absolute ethanol, and 200 ml of ether are added. The mixture is left to stand at 4° C. overnight, the precipitate is filtered off with suction, and the filtrate is concentrated. The resulting oil is dissolved in 150 ml of methanol. To this are added 36 g (0.22 mole) of HOObt and 200 ml of diethyl ether, and the salt is left to crystallize out at 4° C. The precipitate is filtered off with suction and washed with ether.

Yield: 44 g, melting point 178°-179° C., $[\alpha]_D^{23} = +8.8°$ (c=1 in methanol).

(b) Z-Arg(Z$_2$)-Leu-ol 6.6 g of DCC are added, at 0° C., to a solution of 17.3 g of Z-Arg(Z$_2$)—OH and 8.4 g of H-Ile-ol. HOObt in 200 ml of dimethylformamide. The mixture is stirred at 0° C. for two hours and is left to stand at room temperature for about ten hours. The precipitate is filtered off with suction and discarded. The filtrate is concentrated, and the residue is triturated with saturated aqueous NaHCO$_3$ solution and filtered off with suction, thoroughly washed with water and dried. For purification, the solid is stirred with methanol at room temperature, cooled, filtered off with suction, and dried.

Yield: 17.4 g, melting point 180°-182° C., $[\alpha]_D^{22} = -4.2°$ (c=1 in dimethylformamide).

(c) H-Arg-Leu-ol ditosylate

Pd/carbon catalyst is added to a suspension of 13.5 g of Z-Arg(Z$_2$)-Leu-ol in 350 ml of methanol and, at pH 4.5 with addition of 1M p-toluenesulfonic acid (autotitrator), hydrogen is passed through. The substance dissolves during the hydrogenation. After the reaction is complete (no more p-toluenesulfonic acid solution is consumed), the catalyst is filtered off with suction, and the filtrate is concentrated. The residue is stirred with water. Insolubles are filtered off with suction and discarded. The filtrate is concentrated, and the residue is triturated with ether. The precipitate is filtered off with suction and dried.

Yield: 9.95 g, amorphous substance, $[\alpha]_D^{22} = +1.8°$ (c=1 in methanol).

(d) Z-Asp(OtBu)-Arg-Leu-ol tosylate 1.99 ml of N-ethylmorpholine and 5.85 g of Z-Asp(OtBu)-ONSu are added to a solution of 8.6 g of H-Arg-Leu-ol ditosylate in 100 ml of dimethylformamide. The mixture is left to stand at room temperature overnight. The solution is concentrated in vacuo, and the residue is dissolved in n-pentanol. The solution is extracted twice by shaking with water. The organic phase is concentrated, and the residue is triturated with ether. The precipitate is filtered off with suction.

Yield: 9.05 g, amorphous substance, $[\alpha]_D^{22} = -26.2°$ (c=1 in methanol).

(e) H-Asp(OtBu)-Arg-Leu-ol ditosylate 7.5 g of Z-Asp(OtBu)-Arg-Leu-ol tosylate are dissolved in 150 ml of methanol and catalytically hydrogenated in analogy to Example 2c.

Yield: 7.47 g, amorphous substance, $[\alpha]_D^{22} = -7.4°$ (c=1 in methanol).

(f) Z-Arg-Ile-Asp(OtBu)-Arg-Leu-ol ditosylate 440 mg of DCC are added, at 0° C., to a solution of 843 mg of Z-Arg-Ile-OH, 1.58 g of H-Asp(OtBu)-Arg-Leu-ol ditosylate and 326 mg of HOObt in 20 ml of dimethylformamide. The mixture is stirred at 0° C. for 1 hour and at room temperature for 2 hours. After standing at 4° C. overnight, the next day the precipitate is filtered off with suction. The precipitate is discarded, and the filtrate is concentrated in vacuo. The residue is subjected to countercurrent partition between 80 ml of acetic acid and 80 ml of water (5 stages). The fractions containing the title compound are concentrated and finally freeze-dried.

Yield: 1.89 g amorphous substance, $[\alpha]_D^{20} = -29.5°$ (c=1 in methanol).

(g) H-Arg-Ile-Asp(OtBu)-Arg-Leu-ol ditosylate is dissolved in 30 ml of 90% acetic acid and catalytically hydrogenated in analogy to Example 1b. For conversion into the acetate, the residue is stirred in aqueous solution with a weakly basic ion exchanger (in the acetate form). The exchanger is filtered off with suction, and the filtrate is freeze-dried.

Yield: 1.04 g $[\alpha]_D^{23} = -34.7°$ (c=1 in water).

EXAMPLE 3

H-Arg-Ile-Asp(OtBu)-Arg-Ile-ol

The compounds were prepared in analogy to Example 2.

(a) H-Ile-ol.HOObt

Melting point 178°–179° C., $[\alpha]_D^{23} = 8.8°$ (c=1 in methanol).

(b) Z-Arg(Z$_2$)-Ile-ol
Melting point 180°–182° C., $[\alpha]_D^{22} = -4.2°$ (c=1 in dimethylformamide).

(c) H-Arg-Ile-ol ditosylate
Amorphous substance, $[\alpha]_D^{22} = +7.9°$ (c=1 in methanol).

(d) Z-Asp(OtBu)-Arg-Ile-ol tosylate
Amorphous substance, $[\alpha]_D^{23} = -22.2°$ (c=1 in methanol).

(e) H-Asp(OtBu)-Arg-Ile-ol ditosylate
Amorphous substance, $[\alpha]_D^{22} = -4.2°$ (c=1 in methanol).

(f) Z-Arg-Ile-Asp(OtBu)-Arg-Ile-ol ditosylate
Amorphous substance, $[\alpha]_D^{23} = -26.1°$ (c=1 in methanol).

(g) H-Arg-Ile-Asp(OtBu)-Arg-Ile-ol triacetate
Amorphous substance, $[\alpha]_D^{23} = -31.7°$ (c=1 in water).

EXAMPLE 4

H-Arg-Ile-Asp(OtBu)-Arg-isobutylamide

The compounds were prepared in analogy to Example 2.

(a) Z-Arg(Z$_2$)-isobutylamide
Melting point 148°–149° C., $[\alpha]_D^{22} = +7.7°$ (c=1 in dimethylformamide).

(b) H-Arg-isobutylamide ditosylate
Amorphous substance, $[\alpha]_D^{22} = +13.3°$ (c=1 in methanol).

(c) Z-Asp(OtBu)-Arg-isobutylamide tosylate
Amorphous substance, $[\alpha]_D^{23} = -21.0°$ (c=1 in methanol).

(d) H-Asp(OtBu)-Arg-isobutylamide ditosylate
Amorphous substance, $[\alpha]_D^{22} = -1.6°$ (c=1 in methanol).

(e) Z-Arg-Ile-Asp(OtBu)-Arg-isobutylamide ditosylate
Amorphous substance, $[\alpha]_D^{20} = -22.9°$ (c=1 in methanol).

(f) H-Arg-Ile-Asp(OtBu)-Arg-isobutylamide triacetate
Amorphous substance, $[\alpha]_D^{23} = -28.5°$ (c=1 in water).

EXAMPLE 5

H-Arg-Ile-Asp(OtBu)-Arg-Ile-NH$_2$

The compounds were prepared in analogy to Example 2:

(a) Z-Arg(Z$_2$)-Ile-NH$_2$
Melting point 178°–188° C., $[\alpha]_D^{22} = +3.5°$ (c=1 in dimethylformamide).

(b) H-Arg-Ile-NH$_2$ ditosylate
Amorphous substance, $[\alpha]_D^{22} = +9.8°$ (c=1 in methanol).

(c) Z-Asp(OtBu)-Arg-Ile-NH$_2$ tosylate
Amorphous substance, $[\alpha]_D^{23} = -18.0°$ (c=1 in methanol).

(d) H-Asp(OtBu)-Arg-Ile-NH$_2$ ditosylate
Amorphous substance, $[\alpha]_D^{22} = -3.3°$ (c=1 in methanol).

(e) Z-Arg-Ile-Asp(OtBu)-Arg-Ile-NH$_2$ ditosylate
Amorphous substance, $[\alpha]_D^{20} = -26.0°$ (c=1 in methanol).

(f) H-Arg-Ile-Asp(OtBu)-Arg-Ile-NH$_2$ triacetate
Amorphous substance, $[\alpha]_D^{23} = -34.33°$ (c=1 in water).

EXAMPLE 6

H-Arg-Ile-Asp(OtBu)-Arg-Val-NH$_2$

The substances were prepared in analogy to Example 2.

(a) Z-Arg(Z$_2$)-Val-NH$_2$
Melting point 174°–178° C., $[\alpha]_D^{22} = +4.6°$ (c=1 in dimethylformamide).

(b) H-Arg-Val-NH$_2$ ditosylate
Amorphous substance, $[\alpha]_D^{22} = +11.8°$ (c=1 in methanol).

(c) Z-Asp(OtBu)-Arg-Val-NH$_2$ tosylate
Amorphous substance, $[\alpha]_D^{23} = 16.5°$ (c=1 in methanol).

(d) H-Asp(OtBu)-Arg-Val-NH$_2$ ditosylate
Amorphous substance, $[\alpha]_D^{22} = 2.7°$ (c=1 in methanol).

(e) Z-Arg-Ile-Asp(OtBu)-Arg-Val-NH$_2$ ditosylate
Amorphous substance, $[\alpha]_D^{23} = -24.3°$ (c=1 in methanol).

(f) H-Arg-Ile-Asp(OtBu)-Arg-Val-NH$_2$ triacetate
Amorphous substance, $[\alpha]_D^{23} = -36.2°$ (c=1 in water).

EXAMPLE 7

H-Arg-Ile-Asp(OtBu)-Arg-Trp—NH$_2$

The substances were prepared in analogy to Example 2.

(a) Z-Arg(Z$_2$)-Trp—NH$_2$
Melting point 172°–174° C., $[\alpha]_D^{22} = -1.4°$ (c=1 in dimethylformamide).

(b) H-Arg-Trp-NH$_2$ ditosylate
Amorphous substance, $[\alpha]_D^{22} = +13.5°$ (c=1 in methanol).

(c) Z-Asp(OtBu)-Arg-Trp-NH$_2$ ditosylate
Amorphous substance, $[\alpha]_D^{23} = -18.2°$ (c=1 in methanol).

(d) H-Asp(OtBu)-Arg-Trp-NH$_2$ ditosylate
Amorphous substance, $[\alpha]_D^{22} = -3.2°$ (c=1 in methanol).

(e) Z-Arg-Ile-Asp(OtBu)-Arg-Trp-NH$_2$ ditosylate
Amorphous substance, $[\alpha]_D^{20} = -25.0°$ (c=1 in methanol).

(f) H-Arg-Ile-Asp(OtBu)-Arg-Trp-NH$_2$ triacetate
Amorphous substance, $[\alpha]_D^{23} = -31.9°$ (c=1 in water).

EXAMPLE 8

H-Arg-Pro-Val-Lys-Val-OH (a) H-Lys(Boc)-Val-OtBu.HCl
1.3 ml of N-ethylmorpholine and 2.2 g of DCC are added, at 0° C., to a stirred solution of 4.5 g of Z-Lys(Boc)-OH, 2.1 g H-Val-OtBu.HCl and 1.35 g of HOBt in 20 ml of dimethylformamide. The mixture is left to stir at 0° C. for one hour and then to stand at room temperature overnight. The precipitate is filtered off with suction and discarded. The filtrate is concentrated in vacuo. The residue is partitioned between ethyl acetate and water. The ethyl acetate phase is washed successively with KHSO$_4$/K$_2$SO$_4$ buffer, saturated aqueous NaHCO$_3$ solution and water, dried over Na$_2$SO$_4$, and concentrated. Purification: chromatography on silica gel in CH$_2$Cl$_2$/acetone/petroleum ether 9:0.5:2.

Yield: 3.7 g of oily substance.

The above substance is catalytically hydrogenated (Pd/BaSO$_4$) in methanol at pH 4.5 (autotitrator: addition of 1 N methanolic HCl). After hydrogenation is complete, the catalyst is filtered off with suction, and the filtrate is concentrated. The residue is subjected to countercurrent partition between n-pentanol and aqueous NaCl solution (5 stages). The first pentanol fraction is concentrated, and the residue is triturated with ether.

Yield: 1.25 g, melting point 141°–143° C., $[\alpha]_D^{21} = -1.7°$ (c=1 in methanol).

(b) Z-Pro-Val-OtBu 1.3 ml of N-ethylmorpholine and 2.2 g of DCC are added, at 0° C., to a solution of 2.49 g of Z-Pro-OH, 2.1 g of H-Val-OtBu.HCl and 1.35 g of HOBt in 20 ml of dimethylformamide. The subsequent procedure is as in Example 8a. The residue is triturated with petroleum ether, filtered off with suction and dried.

Yield: 2.83 g, melting point 110°–112° C., $[\alpha]_D^{21} = -66.6°$ (c=1 in methanol).

(c) Z-Pro-Val-OH 2.63 g of Z-Pro-Val-OtBu are dissolved in 20 ml of 90% trifluoroacetic acid. The mixture is left to stand at room temperature for one hour, and is concentrated. The residue is triturated with water. The precipitate is filtered off with suction and dried over $P_2O_5$. For further purification, the product is chromatographed on silica gel in $CH_2Cl_2/CH_3OH$/petroleum ether/acetic acid/water 18:1:2:0.1:0.1.

Yield: 1.2 g, melting point 131°–133° C., $[\alpha]_D^{22} = -56.9°$ (c=1 in methanol).

(d) Z-Pro-Val-Lys(Boc)-Val-OtBu 0.38 ml of N-ethylmorpholine and 0.66 g of DCC are added, at 0° C., to a solution of 1.05 g of Z-Pro-Val-OH, 1.3 g of H-Lys(Boc)-Val-OtBu.HCl and 0.5 g of HOObt in 5 ml of dimethylformamide. The mixture is stirred at 0° C. for one hour and left to stand at room temperature overnight. The working-up is as in Example 8a. The residue is triturated with ether. The precipitate is filtered off with suction and dried.

Yield: 1.45 g, melting point 139°–141° C., $[\alpha]_D^{22} = +75 \ 1°$ (c=1 in methanol).

(e) H-Pro-Val-Lys(Boc)-Val-OtBu.HCl 1.32 g of Z-Pro-Val-Lys(Boc)-Val-OtBu are catalytically hydrogenated in analogy to Example 8a.

Yield: 1 g, melting point 150°–157° C., $[\alpha]_D^{23} = -52.2°$ (c=1 in methanol).

(f) Z-Arg(ZP)-Pro-Val-Lys(Boc)-Val-OtBu 0.18 ml of N-ethylmorpholine and 0.31 g of DCC are added at 0° C., to a solution of 0.89 g of H-Pro-Val-Lys(Boc)i Val-OtBu.HCl, 0.81 g of Z-Arg($Z_2$)—OH and 0.23 g of HOObt in 10 ml of dimethylformamide, and the process is continued as in Example 8a. The residue crystallizes on trituration with ether.

Yield 1.02 g, melting point 86°–92° C., $[\alpha]_D^{23} = -56.3°$ (c=1 in methanol).

(g) H-Arg-Pro-Val-Lys-Val-OH diacetate 0.9 g of Z-Arg($Z_2$)-Pro-Val-Lys(Boc)-Val-OtBu is suspended in 90% acetic acid and catalytically hydrogenated in analogy to Example 1b. The residue which is insoluble in ether (0.55 g) is dissolved in 5 ml of 90% trifluoroacetic acid. The mixture is left to stand at room temperature for one hour and is concentrated. The residue is taken up in water, and the solution is stirred with a weakly basic ion exchanger (in the acetate form). The ion exchanger is filtered off with suction, and the filtrate is freeze-dried. Purification: chromatography on a cross-linked dextran gel.

Yield: 306.3 mg, $[\alpha]_D^{24} = +89.5°$ (c=1 in water).

EXAMPLE 9

H-D-Arg-Ile-Leu-Arg-Ile-OH (a) Z-D-Arg-Ile-OBzl 6.6 g of DCC are added, at 0° C., to a solution of 9.25 g of Z-D-Arg-H, 11,8 g of H-Ile-OBzl tosylate and 4.05 g of HOBt in 150 ml of dimethylformamide. The mixture is stirred at 0° C. for one hour and left to stand at room temperature overnight. The precipitate is filtered off with suction and discarded. The filtrate is concentrated, and the residue is partitioned between ethyl acetate and saturated aqueous $NaHCO_3$ solution. The ethyl acetate phase is washed with water, dried over $Na_2SO_4$ and concentrated. The residue is triturated with ether. The solution is decanted off, and the residue is triturated with petroleum ether. The precipitate is filtered off with suction and dried.

Yield: 19.5 g; $[\alpha]_D^{25} = -2.7°$ (c=1 in methanol).

(b) Z-D-Arg-Ile-OH 41.8 ml of aqueous 1N NaOH are added to a solution of 19 g of Z-D-Arg-Ile-OBzl in a mixture of 70 ml of dioxane, 30 ml of water and 12 ml of methanol, and the mixture is left to stand at room temperature overnight. The next day it is neutralized with about 3.3 ml of 4N HCl. The cloudy solution is filtered with suction through a clarifying layer, and the filtrate is concentrated. The residue is partitioned between 120 ml of n-pentanol and 120 ml of water. The aqueous phase is extracted a further 4 times by shaking with n-pentanol. The n-pentanol phases are concentrated together. The residue is triturated with ethyl acetate, and the precipitate is filtered off with suction.

Yield: 8.4 g, $[\alpha]_D^{22} = +12.3°$ (c=1 in 90% acetic acid).

(c) Fmoc-Leu-OObt 2.06 g of DCC are added to a solution of 3.53 g of FmocI Leu—OH and 1.63 g of HOObt in 40 ml of $CH_2Cl_2$. The mixture is stirred at 0° C. for one hour and left to stand at room temperature overnight. The precipitate is filtered off with suction and discarded. The filtrate is concentrated, and the residue is triturated twice with petroleum ether and dried under high vacuum.

Yield: 5.2 g of amorphous substance.

(d) Fmoc-Leu-Arg-OH 5 g of Fmoc-Leu-OObt are added, at room temperature, to a mixture of 1.74 g of arginine, 1.63 g of HOObt and 1.79 g of pyridinium perchlorate in 50 ml of dimethylformamide. The mixture is stirred at room temperature for 3 hours and left to stand at room temperature overnight. The clear solution is concentrated, and water is added to the residue. The pH is adjusted to 7 with aqueous $NaHCO_3$ solution. The precipitate is filtered off with suction, washed with water and dried.

Yield 4.7 g, melting point 145°–155° C. (with decomposition), $[\alpha]_D^{23} = -18.5°$ (c=1 in methanol).

(e) Fmoc-Leu-Arg-Ile-OBzl 880 mg of DCC are added, at 0° C., to a solution of 2.04 g of Fmoc-Leu-Arg-OH, 1.57 g of H-Ile-OBzl tosylate and 0.65 g of HOObt in 20 ml of dimethylformamide. The mixture is stirred at 0° C. for one hour and left to stand at room temperature overnight. The precipitate is filtered off with suction and discarded. The filtrate is concentrated, and the residue is partitioned between ethyl acetate and saturated aqueous $NaHCO_3$ solution. The ethyl acetate phase is further extracted by shaking twice with saturated aqueous $NaHCO_3$ solution and 3 times with water, dried over $Na_2SO_4$ and concentrated. The residue is triturated with ether and filtered off with suction.

Yield: 2.59 g $[\alpha]_D^{24} = -36.4°$ (c = 1 in methanol).

(f) Z-D-Arg-Ile-Leu-Arg-Ile-OBzl diacetate 3.25 ml of diethylamine are added to a solution of 2.18 g of Fmoc-Leu-Arg-Ile-OBzl in 15 ml of dimethylformamide. The mixture is left to stir at room temperature for 15 minutes, and is concentrated. The residue is dissolved in 125 ml of n-pentanol, and the solution is extracted by shaking with a half-concentrated aqueous $NaHCO_3$ solution. The n-pentanol phase is concentrated, and the residue is triturated with ether and filtered off with suction.

Yield: 1.4 g of H-Leu-Arg-Ile-OBzl.

220 mg of DCC are added, at 0° C., to a solution of 421.5 mg of Z-D-Arg-Ile-OH, 490.6 mg of H-Leu-Arg-Ile-OBzl, 179.5 mg of pyridinium perchlorate and 163 mg of HOObt in 10 ml of dimethylformamide. The mixture is stirred at 0° C. for one hour and left to stand at room temperature overnight. The precipitate is filtered off with suction and discarded. The filtrate is concentrated, and the residue is dissolved in 50 ml of n-pentanol. The solution is extracted by shaking twice with 50 ml of half-concentrated aqueous $NaHCO_3$ solution each time, and is concentrated. The residue is triturated with acetic acid and is filtered off with suction.

Yield: 856 mg.

For purification, the substance is subjected to countercurrent partition between 45 ml of 10% aqueous acetic acid and 45 ml of ethyl acetate. The aqueous phases 1-4 are concentrated, and the residue is triturated with ether and filtered off with suction.

Yield: 620 mg, amorphous substance, $[\alpha]_D^{23} = -31.3°$ (c = 1 in methanol).

(g) H-D-Arg-Ile-Leu-Arg-Ile-OH diacetate 510 mg of Z-D-Arg-Ile-Leu-Arg-Ile-OBzl are catalytically hydrogenated in 15 ml of 90% acetic acid in analogy to Example 1b.

Yield: 445 mg, $[\alpha]_D^{21} = -66.2°$ (c = 1 in water)

EXAMPLE 10

H-Arg-Ile-Leu-D-Arg-Ile-OH (a) Fmoc-Leu-D-Arg-OH

The substance is prepared in analogy to Example 9d. Melting point 145°-155° C. (with decomposition), $[\alpha]_D^{23} = -31.3°$ (c = 1 in methanol).

(b) Fmoc-Leu-D-Arg-Ile-OBzl

The substance is prepared in analogy to Example 9e. $[\alpha]_D^{24} = -9.8°$ (c = 1 in methanol).

(c) Z-Arg-Ile-Leu-D-Arg-Ile-OBzl diacetate

The substance is prepared in analogy to Example 9f. Amorphous substance, $[\alpha]_D^{23} = -18.3°$ (c = 1 in methanol).

(d) H-Arg-Ile-Leu-D-Arg-Ile-OH diacetate

The substance is prepared in analogy to Example 9g. Amorphous substance, $[\alpha]_D^{24} = -14.0°$ (c = 1 in water).

EXAMPLE 11

H-Arg-Ile-Leu-Arg-D-Val-OH (a) Fmoc-Leu-Arg-D-Val-OBzl

The substance is prepared in analogy to Example 9e. Amorphous substance, $[\alpha]_D^{24} = -18.3°$ (c = 1 in methanol).

(b) Z-Arg-Ile-Leu-Arg-D-Val-OBzl diacetate

The substance is prepared in analogy to Example 9f. Amorphous substance, $[\alpha]_D^{23} = -24.2°$ (c = 1 in methanol).

(c) H-Arg-Ile-Leu-Arg-D-Val-OH diacetate

The substance is prepared in analogy to Example 9g. Amorphous substance, $[\alpha]_D^{20} = -37.1°$ (c = 1 in water).

EXAMPLE 12

H-Arg-Ile-D-Leu-Arg-D-Val-OH (a) Fmoc-D-Leu-Arg-OH

The substance is prepared in analogy to Example 9d. Melting point 140°-150° C. (with decomposition), $[\alpha]_D^{23} = +30.8°$ (c = 1 in methanol).

(b) Fmoc-D-Leu-Arg-D-Val-OBzl

The substance is prepared in analogy to Example 9e. Amorphous substance, $[\alpha]_D^{24} = +11.2°$ (c = 1 in methanol).

(c) Z-Arg-Ile-D-Leu-Arg-D-Val-OBzl diacetate

The substance is prepared in analogy to Example 9f. Amorphous substance, $[\alpha]_D^{22} = +5.2°$ (c = 1 in methanol).

(d) H-Arg-Ile-D-Leu-Arg-D-Val-OH diacetate

The substance is prepared in analogy to Example 9g. Amorphous substance, $[\alpha]_D^{22} = +10.6°$ (c = 1 in water).

EXAMPLE 13

H-D-Arg-Ile-D-Leu-Arg-Ile-OH (a) Fmoc-D-Leu-Arg-Ile-OBzl

The substance is prepared in analogy to Example 9e. Amorphous substance, $[\alpha]_D^{24} = -5.7°$ (c = 1 in methanol).

(b) Z-D-Arg-Ile-D-Leu-Arg-Ile-OBzl diacetate

The substance is prepared in analogy to Example 9f. Amorphous substance, $[\alpha]_D^{24} = -2.4°$ (c = 1 in methanol).

(c) H-D-Arg-Ile-D-Leu-Arg-Ile-OH diacetate

The substance is prepared in analogy to Example 9g. Amorphous substance, $[\alpha]_D^{23} = -20.3°$ (c = 1 in water).

EXAMPLE 14

H-D-Arg-D-allo-Ile-D-Leu-Arg-Ile-OH diacetate

On purification of H-D-Arg-Ile-D-Leu-Arg-Ile-OH by column chromatography there was isolated a fraction which, according to amino acid analysis, was H-D-Arg-D-allo-Ile-D-Leu-Arg-Ile-OH. Amorphous substance, amino acid analysis: D-allo-Ile (0.9), Ile (1.06), Leu (1.03), Arg (1.87).

EXAMPLE 15

H-D-Arg-Ile-Leu-D-Arg-Ile-OH (a) Z-D-Arg-Ile-Leu-D-Arg-Ile-OBzl diacetate

The substance is prepared in analogy to Example 9f. Amorphous substance, $[\alpha]_D^{24} = -6.9°$ (c = 1 in methanol).

(b) H-D-Arg-Ile-Leu-D-Arg-Ile-OH diacetate

The substance is prepared in analogy to Example 9g. Amorphous substance, $[\alpha]_D^{23} = -30.5°$ (c = 1 in water).

EXAMPLE 16

H-Arg-D-Val-Leu-Arg-Ile-OH (a) Z-Arg-D-Val-OBzl

The substance is prepared in analogy to Example 9a.

Amorphous substance, $[\alpha]_D^{25} = +6.2°$ (c=1 in methanol).

(b) Z-Arg-D-Val-OH

The substance is prepared in analogy to Example 9b. $[\alpha]_D^{24} = -6.1°$ (c=1 in 90% acetic acid).

(c) Z-Arg-D-Val-Leu-Arg-Ile-OBzl diacetate

The substance is prepared in analogy to Example 9f. Amorphous substance, $[\alpha]_D^{23} = -30.7°$ (c=1 in methanol).

(d) H-Arg-D-Val-Leu-Arg-Ile-OH diacetate

The substance is prepared in analogy to Example 9g. Amorphous substance, $[\alpha]_D^{19} = -15.1°$ (c=1 in water).

EXAMPLE 17

H-Arg-Ile-Trp-Arg-Ile-OH (a) Z-Arg-Ile-OH

The substance is prepared in analogy to Examples 9a and 9b.
$[\alpha]_D^{22} = -5.9°$ (c=1 in methanol).

(b) Z-Arg(Z$_2$)-Ile-OMe

The substance is prepared in analogy to Example 1a. Melting point 129°-130° C.

(c) H-Arg-Ile-OMe ditosylate

The substance is prepared by catalytic hydrogenation of Z-Arg(Z$_2$)-Ile-OMe in analogy to Example 2c.

Amorphous substance, $[\alpha]_D^{22} = +8.4°$ (c=1 in methanol).

(d) Z-Trp-Arg-Ile-OMe tosylate

The substance is prepared in analogy to Example 2d. Amorphous substance, $[\alpha]_D^{22} = -20.6°$ (c=1 in methanol).

(e) H-Trp-Arg-Ile-OMe ditosylate

The substance is prepared in analogy to Example 2e. Amorphous substance, $[\alpha]_D^{22} = -4.5°$ (c=1 in methanol).

(f) Z-Arg-Ile-Trp-Arg-Ile-OMe ditosylate

The substance is prepared in analogy to Example 2f. Amorphous substance, $[\alpha]_D^{22} = -27.5°$ (c=1 in methanol).

(g) Z-Arg-Ile-Trp-Arg-Ile-OH tosylate

Aqueous NaOH is added dropwise to a stirred solution of 2.7 g of Z-Arg-Ile-Trp-Arg-Ile-OMe in 30 ml of dioxane, 10 ml of water and 4 ml of methanol until the pH is 13.5. A total of 5.2 ml of 1N NaOH was consumed. The solution is adjusted to pH 7.8 with 0.82 ml of aqueous 1N p-toluenesulfonic acid solution, and is concentrated in vacuo. The residue is dissolved in n-butanol, and the solution is extracted 3 times with water. The combined aqueous phases are extracted once with n-butanol. The combined n-butanol phases are concentrated. The residue is dissolved in ethanol, and the solution is added dropwise to a mixture of ethyl acetate and ether.

Yield: 1.59 g, $[\alpha]_D^{22} = -25.2°$ (c=1 in methanol).

(h) ditosylate

The compound is prepared by catalytic hydrogenation of Z-Arg-Ile-Trp-Arg-Ile-OH tosylate in analogy to Example 2c. 5 Amorphous substance, $[\alpha]_D^{22} = -10.5°$ (c=1 in methanol).

The following peptides were also prepared under the same conditions as in Example 17:

Z-Arg-Ile-Leu-Arg-Ile-OMe ditosylate
Z-Arg-Ile-Leu-Arg-Ile-OH tosylate
H-Arg-Ile-Leu-Arg-Ile-OH ditosylate
Z-Arg-Ile-Phe-Arg-Ile-OMe- ditosylate
Z-Arg-Ile-Phe-Arg-Ile-OH tosylate
H-Arg-Ile-Phe-Arg-Ile-OH ditosylate
Z-Arg-Ile-Ser(tBu)-Arg-Ile-OMe ditosylate
Z-Arg-Ile-Ser(tBu)-Arg-Ile-OH tosylate
H-Arg-Ile-Ser(tBu)-Arg-Ile-OH ditosylate
Z-Arg-Ile-D-Ser(tBu)-Arg-Ile-OMe ditosylate
Z-Arg-Ile-D-Ser(tBu)-Arg-Ile-OH tosylate
H-Arg-Ile-D-Ser(tBu)-Arg-Ile-OH distosylate.

In each case, amino acid analysis is consistent with the expected values.

EXAMPLE 18 cyclo(Gly-Arg-Ile-Phe-Arg-Ile)

78 mg of Boc-Gly-OTcp, 3 mg of HOBt and 0.026 ml of N-ethylmorpholine are added, at room temperature, to a solution of 210 mg of H-Arg-Ile-Phe-Arg-Ile-OH ditosylate in 3 ml of dimethylformamide. The mixture is stirred at room temperature for a few hours and is left to stand at room temperature overnight. The mixture is concentrated in vacuo, and the residue is partitioned between water and ethyl acetate to which a little ethanol has been added. The ethyl acetate phase is extracted once more with water. The combined aqueous phases are extracted with ethyl acetate. The combined aqueous phases are concentrated. The residue (Boc-Gly-Arg-Ile-Phe-Arg-Ile-OH tosylate) is dissolved in 2 ml of trifluoroacetic acid. After 45 minutes at room temperature, the solution is concentrated and again distilled twice with ether. There remain 200 mg of a resin (H-Gly-Arg-Ile-Phe-Arg-Ile-OH tosylate trifluoroacetate), which is dissolved in 200 ml of dimethylformamide. To this solution is added 0.1 ml of a 50% solution of ethylmethylphosphinic anhydride in $CH_2Cl_2$ and, with stirring, slowly a solution of 0.16 ml of N-ethylmorpholine in 5 ml of dimethylformamide. The mixture is stirred at room temperature for 2.5 hours and, after addition of a little water, is concentrated in vacuo. The residue is dissolved in a little isopropanol, and the solution is added dropwise to stirred ether.

Yield: 60 mg. The FAB mass spectrum shows the expected molecular mass of 743.

EXAMPLE 19 cyclo(Gly-Arg-Ile-Leu-Arg-Ile)

The compound is prepared from H-Arg-Ile-Leu-Arg-Ile-OH ditosylate in analogy to Example 18. The FAB mass spectrum shows the expected molecular mass of 708.

EXAMPLE 20

H-Arg-Leu-Gln-Arg-Leu—OH (a) H-Arg-Leu-OtBu.2 HCl 3.9 ml of N-ethylmorpholine and 22.7 g of Z-Arg(Z$_2$)-OTcp are added, at room temperature, to a solution of 6.7 g of H-LeuOtBu.HCl and 4.05 g of HOBt in 50 ml of dimethyl-formamide. After a reaction time of two hours, 300 ml of ice-water are added to the mixture. The precipitate is filtered off with suction, triturated with saturated aqueous NaHCO$_3$ solution, again filtered off with suction, and washed with water and dried.

Yield: 27.4 g of Z-Arg(Z$_2$)-Leu-OtBu. The substance obtained above is catalytically hydrogenated in analogy to Example 8a.

Yield: 11.6 g, $[\alpha]_D^{23} = -4.0°$ (c=1 in methanol).

(b) H-Arg-Leu-Gln-Arg-Leu—OH diacetate 0.52 ml of N-ethylmorpholine and 880 mg of DCC are added, at 0° C., to a solution of 3.27 g of Z-Arg(Z$_2$)-Leu-Gln-H, 1.66 g of H-Arg-Leu-OtBu.2 HCl and 652 mg of HOObt in 50 ml of dimethylformamide. The mixture is stirred at 0° C. for one hour and at room temperature for one hour and is left to stand at room temperature overnight. The precipitate is filtered off with suction. The peptide is precipitated from the filtrate with half-saturated aqueous NaHCO$_3$ solution. The precipitate (Z-Arg(Z$_2$)-Leu-Gln-Arg-Leu-OtBu) is filtered off with suction and washed with water and dried. The substance obtained above is catalytically hydrogenated in 90% acetic acid in analogy to Example 1b.

Yield: 3.7 g of H-Arg-Leu-Gln-Arg-Leu-OtBu triacetate.

300 mg of the H-Arg-Leu-Gln-Arg-Leu-OtBu triacetate are dissolved in 3 ml of 90% trifluoroacetic acid. The solution is left to stand at room temperature for one hour and is concentrated in vacuo. The residue is dissolved in water, and the solution is stirred with a weakly basic ion exchanger (acetate form) until the pH has become about 4. The ion exchanger is filtered off with suction, and the filtrate is freeze-dried.

Yield: 258.8 mg, $[\alpha]_D^{23} = -28.9$ ° (c=1 in water).

EXAMPLE 21

H-Arg-Val-Tyr-Arg-Pro-OH (a) Z-Tyr(tBu)-Arg-Pro-OtBu

H-Arg-Pro-OtBu ditosylate is prepared in analogy to Example 20a and Example 2c.

0.66 ml of N-ethylmorpholine and 1.12 g of DCC are added, at 0° C., to a solution of 3.4 g of H-Arg-Pro-OtBu ditosylate, 1.9 g of Z-Tyr(tBu)—OH and 0.69 g of HOBt in 15 ml of dimethylformamide. The mixture is left to stir at 0° C. for one hour and is then left at room temperature overnight. The precipitate is filtered off with suction and discarded. The filtrate is concentrated, and the residue is partitioned between ethyl acetate and saturated aqueous NaHCO$_3$ solution. The ethyl acetate phase is extracted by shaking once more with saturated aqueous NaHCO$_3$ solution and once with water, and is dried over Na$_2$SO$_4$ and concentrated. The residue is triturated with petroleum ether and filtered off with suction.

Yield: 3.35 g, melting point 115°–125° C. (with decomposition), $[\alpha]_D^{24} = -35.8°$ (c=1 in methanol).

(b) H-Tyr(tBu)-Arg-Pro-OtBu ditosylate

The substance is prepared in analogy to Example 2c. Melting point 105°–110° C. (with decomposition), $[\alpha]_D^{24}$32 $-20.7°$ (c=1 in methanol).

(c) Z-Arg(Z$_2$)-Val-OtBu 1.3 ml of N-ethylmorpholine and 2.2 g of DCC are added, at 0° C., to a solution of 5.77 g of Z-Arg(Z$_2$)—OH, 2.1 g of H-Val-OtBu.HCl and 1.63 g of HOObt in 20 ml of dimethylformamide. The subsequent procedure is as in Example 1a.

Yield: 4.55 g, melting point 103°–105° C., $[\alpha]_D^{24} = +9.2°$ (c=1 in methanol).

(d) Z-Arg(Z$_2$)-Val-OH 4.5 g of Z-Arg(Z$_2$)-Val-OtBu are dissolved in about 45 ml of 90% trifluoroacetic acid. The solution is left to stand at room temperature for one hour, and is concentrated. The residue is triturated with ether and is filtered off with suction.

Yield: 3.58 g, melting point 142°–144° C., $[\alpha]_D^{22} = +1.1°$ (c=1 in methanol).

(e) Z-Arg(Z$_2$)-Val-Tyr(tBu)-Arg-Pro-OtBu 0.4 ml of N-ethylmorpholine and 0.68 g of DCC are added, at 0° C., to a solution of 2.8 g of H-Tyr(tBu)-Arg-Pro-OtBu ditosylate, 2.1 g of Z-Arg(Z$_2$)-Val-OH and 0.5 g of HOObt in 10 ml of dimethylformamide. The mixture is stirred at 0° C. for one hour and left to stand at room temperature overnight. The precipitate is filtered off with suction and discarded. The filtrate is concentrated in vacuo. The residue is partitioned between ethyl acetate and water. This results in precipitation of a substance which is filtered off with suction. This substance is triturated twice with saturated aqueous NaHCO$_3$ solution and once with water, filtering with suction each time. The substance is recrystallized from ethyl acetate.

Yield: 2.6 g, melting point 141°–147° C., $[\alpha]_D^{23} = -41.8°$ (c=1

(f) H-Arg-Val-Tyr(tBu)-Arg-Pro-OtBu triacetate 2.4 g of Z-Arg(Z$_2$)-Val-Tyr(tBu)-Arg-Pro-OtBu are catalytically hydrogenated in analogy to Example 1b.

Yield after purification on a dextran gel: 1.172 g, $[\alpha]_D^{23}$ ° (c=1 in water).

(g) H-Arg-Val-Tyr-Arg-Pro-OH diacetate 670 mg of H-Arg-Val-Tyr(tBu)-Arg-Pro-OtBu triacetate are dissolved in a mixture of 10 ml of 90% trifluoroacetic acid and 1 ml of ethyl mercaptan. The solution is left to stand at room temperature for one hour, and is concentrated in vacuo. The residue is partitioned between water and tert.butyl methyl ether. The aqueous phase is stirred with a weakly basic ion exchanger (acetate form) until the pH has become 3.5–4.0. The ion exchanger is filtered off with suction, and the filtrate is freeze-dried.

Yield after purification on a dextran gel: 310 mg. Amino acid analysis showed the calculated values.

EXAMPLE 22

H-Lys-Ile-Asp(OtBu)-Arg-Ile-NH$_2$ ditosylate (a) Z-Lys(Z)-Ile-OMe 29.8 g of Z-Lys(Z)—OH.DCHA and 9.08 g of H-Ile-OMe.HCl are dissolved in DMF and, after 15 min., the precipitated DCHA.HCl is filtered off with suction. To the filtrate are added 10.1 g of HOBt and, at 0° C., 10.8 g of DCC. The mixture is left to reaction at 0° C. for 1 hour and at room temperature for a further hour, and then the solvent is removed in vacuo. The residue is taken up in acetic acid, the urea is removed by filtration, and the filtrate is extracted by shaking successively with aqueous NaHCO$_3$ and NaCl solutions. The organic phase is dried over MgSO$_4$ and concentrated, and the residue is recrystallized from ethyl acetate/hexane.

Yield: 25.1 g, melting point 103°–105° C., $[\alpha]_D^{20} = -13.8°$ (c=1, MeOH).

(b) Z-Lys(Z)-Ile-OH 23.2 g of Z-Lys(Z)-Ile-OMe are dissolved in 150 ml of methanol and, while stirring, 50 ml of 2N aqueous NaOH are added. After reaction is complete, the solvent is removed in vacuo, the residue is dissolved in water, and the solution is extracted with ethyl acetate. The aqueous phase is acidified, while cooling, to pH 2–3 and is extracted with ethyl acetate. The organic phase is washed with water, dried over MgSO$_4$, and the residue obtained after removal of the solvent in vacuo is recrystallized from ethyl acetate/diisopropyl ether.

Yield: 17.5 g, melting point 110°–112° C. (decomposition), $[\alpha]_D^{20} = +2.4°$ (c=1, DMF).

(c) Z-Lys(Z)-Ile-Asp(OtBu)-Arg-Ile-NH$_2$

The preparation is carried out in analogy to Example 2f from the compounds of Examples 22b and 5d. Amorphous substance with correct FAB mass spectrum (967, M+H).

(d) H-Lys-Ile-Asp(OtBu)-Arg-Ile-NHP ditosylate

The preparation is carried out in analogy to Example 2c from the compound of Example 22c. Amorphous substance with correct FAB mass spectrum (699, M+H). $[\alpha]_D^{20} = -23.4°$ (c=1, MeOH).

EXAMPLE 23

H-ε-aminohexanoyl-Ile-Asp(OtBu)-Arg-Ile-NH$_2$ ditosylate

The preparation is carried out in analogy to Example 22.

(a) Z-ε-aminohexanoyl-Ile-OMe

Oily syrup, $[\alpha]_D^{20} = -6.9°$ (c=1, MeOH)

(b) Z-ε-aminohexanoyl-Ile-OH

Melting point 73°–75° C. (decomposition), $[\alpha]_D^{20} = +5.1°$ (c=1, DMF)

(c) Z-ε-aminohexanoyl-Ile-Asp(OtBu)-Arg-Ile-NH$_2$

Amorphous substance with correct FAB mass spectrum (819, M+H)

(d) H-ε-aminohexanoyl-Ile-Asp(OtBu)-Arg-Ile-NH$_2$ ditosylate

Amorphous substance with correct FAB mass spectrum (684, M+H) $[\alpha]_D^{20} = -20.6°$ (c=1, MeOH).

EXAMPLE 24

H-Arg-Ile-Glu(OtBu)-Arg-Ile-NH$_2$ ditosylate acetate

The preparation is carried out in analogy to Example 2.

(a) Z-Glu(OtBu)-Arg-Ile-NH$_2$ tosylate was prepared in analogy to Example 2d.

Amorphous substance with correct NMR spectrum.

(b) H-Glu(OtBu)-Arg-Ile-NH$_2$ ditosylate

The preparation is carried out by catalytic hydrogenation in analogy to Example 2c. The amorphous substance thus obtained was immediately reacted further.

(c) Z-Arg-I-le-Glu(OtBu)-Arg-Ile-NH$_2$ tosylate acetate

The preparation is carried out in analogy to Example 2f from the compound of Example 24b and Z-Arg-Ile-OH. The final purification is carried out by column chromatography on silica gel with CH$_2$Cl$_2$/MeOH/H$_2$O/AcOH (20:7:2:2). Amorphous substance with correct FAB mass spectrum (876, M+H) $[\alpha]_D^{20} = -23.9°$ (c=1, MeOH)

(d) H-Arg-Ile-Glu(OtBu)-Arg-Ile-NH$_2$ ditosylate acetate

The preparation is carried out by catalytic hydrogenation in analogy to Example 2c.

Amorphous substance with correct FAB mass spectrum (741, M+H) $[\alpha]_D^{20} = -15.3°$ (c=1.05; MeOH)

EXAMPLE 25

H-Arg-Ile-Ser(tBu)-Arg-Pro-OtBu (a) Z-Ser(tBu)-Arg-Pro-OtBu tosylate 3.3 g of DCC are added, at 0° C., to a stirred solution of 4.43 g of Z-Ser(tBu)—OH (15 mmol), 10.03 g of H-Arg-Pro-OtBu ditosylate and 2.02 g of HOBt in 40 ml of dimethylformamide. The mixture is worked up in analogy to Example 1a.

Yield 9.8 g, amorphous, $[\alpha]_D^{20} = -49.5°$ (c=1 in methanol).

(b) H-Ser(tBu)-Arg-Pro-OtBu ditosylate 9.2 g of Z-Ser(tBu)-Arg-Pro-OtBu tosylate are catalytically hydrogenated in analogy to Example 2c.

Yield 8.85 g, amorphous, $[\alpha]_D^{20} = -40.8°$ (c=1 in water).

(c) Z-Arg-Ile-Ser(tBu)-Arg-Pro-OtBu diacetate 2.2 g of DCC are added, at 0° C., to a stirred suspension of 4.21 g of Z-Arg-Ile-OH (10 mmol), 8.15 g of H-Ser(tBu)-Arg-Pro-OtBu ditosylate and 1.63 g of HOObt in 50 ml of dimethylformamide. The mixture is stirred at 0° C. for 1 hour and at room temperature for 2 hours, left to stand overnight, and the next day the precipitate is filtered off with suction. The filtrate is concentrated, and the residue is partitioned between n-pentanol and half-concentrated NaHCO$_3$ solution. The pentanol phase is concentrated, and the residue is triturated with ethyl acetate.

Yield 11 g.

The substance obtained above is dissolved in aqueous acetic acid and chromatographed on a weakly basic ion exchanger in the acetate form. The combined peptide-containing eluate is freeze-dried.

Yield 8.75 g 500 mg of the substance obtained above are purified by chromatography on silica gel. A mixture of 1560 ml of n-butanol, 181 ml of acetic acid and 550 ml of water is used for elution.

Yield 251 mg, $[\alpha]_D^{22} = -68.1°$ (c=1 in water).

(d) H-Arg-Ile-Ser(tBu)-Arg-Pro-OtBu triacetate 4.4 g of Z-Arg-Ile-Ser(tBu)-Arg-Pro-OtBu diacetate (crude substance) are dissolved in about 60 ml of 90% strength acetic acid and catalytically hydrogenated in analogy to Example 1b.

Yield 4.25 g.

1 g of the substance obtained above is chromatographed on silica gel. A mixture of 450 ml of methylene chloride, 200 ml of methanol, 150 ml of methylglycol, 100 ml of water and 5 g of ammonium acetate which has been adjusted to pH 6 with glacial acetic acid is used for elution.

Yield 560 mg, amorphous, $[\alpha]_D^{22} = -53.6\ 22°$ (c=1 in water).

EXAMPLE 26

H-Arg-Trp-Asp(OtBu)-Arg-Phe-NH$_2$ (a) Z-Arg(Z$_2$)-Phe-NH$_2$.dicyclohexylurea 3.3 g of DCC are added, at 0° C., to a stirred solution of 8.65 g (15 mmol) of Z-Arg(Z$_2$)—OH, 3.01 g of H-Phe-NH$_2$.HCl, 2.45 g of HOObt and 1.95 ml of N-ethylmorpholine in 30 ml dimethylformamide. The mixture is stirred at 0° C. for 1 hour and then left to stand at room temperature. By the next day the mixture has solidified. The mixture is stirred with half-concentrated NaHCO$_3$ solution, and the solid is filtered off with suction and washed with KHSO$_4$ solution and water.

Yield 13.9 g (the substance still contains an approximately equimolar amount of dicyclohexylurea) $[\alpha]_D^{20} = -2.3°$ (c=1 in 80% strength acetic acid).

(b) H-Asp(OtBu)-Arg-Phe-NHP.2 HClO$_4$ 13.5 g of Z-Arg(Z$_2$)-Phe-NH$_2$.dicyclohexylurea are suspended in 200 ml of dimethylacetamide and catalytically hydrogenated in analogy to Example 2c. In this case, 1N HClO$_4$ is used for titration. The residue is stirred in water. Insolubles are filtered off with suction, and the filtrate is freeze-dried. The resulting oil is triturated twice with diethyl ether and twice with ethyl acetate, decanting each time. The residue is dried under high vacuum.

Yield 9.5 g of oil.

4 g of DCC are added, at 0° C., to a stirred solution of the 9.5 g of oil obtained above, 5.9 g of Z-Asp(OtBu)—OH, 2.48 g of HOBt and 2.37 ml of N-ethylmorpholine in 50 ml of dimethylformamide. Working-up is carried out in analogy to Example 1a. The residue is triturated with diethyl ether and filtered off with suction.

Yield 9.00 g 8.7 g of the substance obtained above [Z-Asp(OtBu)-Arg-PheNH$_2$.HClO$_4$] are catalytically hydrogenated in analogy to Example 2c. In this case 1N HClO$_4$ is used for titration.

Yield 7.8 g, amorphous, $[\alpha]_D^{20} = -4.0°$ (c=1 in methanol).

(c) Z-Trp-Asp(OtBu)-Arg-Phe-NH$_2$.HClO$_4$ 2.2 g of DCC are added, at 0° C., to a stirred solution of 3.4 g (10 mmol) of Z-Trp-OH, 6.92 g of H-Asp(OtBu)-Arg-Phe-NH$_2$.2 HClO$_4$, 1.35 g of HOBt and 1.3 ml of N-ethyl-morpholine in 40 ml of dimethylformamide. The working-up is carried out in analogy to Example 1a.

Yield 7.3 g, amorphous, $[\alpha]_D^{21} = -17.5°$ (c=1 in methanol).

(d) H-Trp-Asp(OtBu)-Arg-Phe-NH$_2$.2 HClO$_4$ 7 g of Z-Trp-Asp(OtBu)-Arg-Phe-NH$_2$ are catalytically hydrogenated in analogy to Example 2c. 1N HClO$_4$ is used for titration.

Yield 6.2 g, amorphous, $[\alpha]_D^{20} = -12.6°$ (c=1 in methanol).

(e) Z-Arg(Z$_2$)-Trp-Asp(OtBu)-Arg-Phe-NH$_2$.HClO$_4$ 220 mg of DCC are added, at 0° C., to a stirred solution of 577 mg (1 mmol) of Z-Arg(Z$_2$)—OH, 879 mg of H-Trp-Asp-(OtBu)-Arg-Phe-NH$_2$.2HClO$_4$, 163 mg of HOObt and 0.13 ml of N-ethylmorpholine in 10 ml of dimethylformamide. The working-up is carried out in analogy to Example 25c. In this case, most of the substance precipitates out of the n-pentanol phase.

Yield 1.16 g, $[\alpha]_D^{20} = -15.2°$ (c=1 in 80% strength aqueous acetic acid).

(f) H-Arg-Trp-Asp(OtBu)-Arg-Phe-NH$_2$ triacetate 3 g of Z-Arg(Z$_2$)-Trp-Asp(OtBu)-Arg-Phe-NH$_2$.HClO$_4$ are catalytically hydrogenated in analogy to Example 1b.

Yield 2.33 g.

960 mg of the substance obtained above are purified by chromatography in analogy to Example 25d.

Yield 540 mg, $[\alpha]_D^{22} = -14.2°$ (c=1 in water).

EXAMPLE 27

H-Lys-Phe-Leu-Lys-Phe-OH (a) Fmoc-Lys(Z)-Phe-OtBu 2.2. g of DCC are added, at 0° C., to a stirred solution of 5.02 g (10 mmol) Fmoc-Lys(Z)—OH, 2.6 g of H-Phe-OtBu. HCl, 1.35 g of HOBt and 1.3 ml of N-ethylmorpholine in 50 ml of dimethylformamide. The working-up is carried out in analogy to Example 1a.

Yield 6.2 g, $[\alpha]_D^{22} = -6.7°$ (c=1 in 90% strength acetic acid).

(b) Fmoc-Lys(Z)-Phe-OH 2.95 g of Fmoc-Lys(Z)-Phe-OtBu are dissolved in 30 ml of 90% strength aqueous trifluoroacetic acid. The solution is left to stand at room temperature for one hour, and is concentrated in vacuo. The residue is triturated with diethyl ether and filtered off with suction.

Yield 2.32 g, $[\alpha]_D^{20} = -2.3°$ (c=1 in methanol).

(c) Fmoc-Lys(Z)-Phe-Lys(Z)-Phe-OtBu 4.7 ml of diethylamine are added to a solution of 3.17 g of Fmoc-Lys(Z)-Phe-OtBu in 20 ml of dimethylformamide. The mixture is left to stand at room temperature for 10 minutes, and is concentrated under high vacuum. The residue is dissolved in methylene chloride, insolubles are filtered off, and the solution is chromatographed on silica gel. Initial elution is with methylene chloride (removal of the lipophilic impurity). The substance is eluted with a 95:5 mixture of methylene chloride and methanol.

Yield 2.3 g.

990 mg of DCC are added, at 0° C., to a solution of the 2.3 g of H-Lys(Z)-Phe-OtBu obtained above, 1.58 g (4.5 mmol) of Fmoc-Leu—OH and 607 mg of HOBt in 20 ml of dimethylformamide. Working-up is carried out in analogy to Example 1a.

Yield 2.7 g. 3.42 ml of diethylamine are added to a solution of the 2.7 g of Fmoc-Leu-Lys(Z)-Phe-OtBu obtained above in 20 ml of dimethylformamide, and the working-up is analogous to that above.

Yield 1.95 g.

720 mg of DCC are added, at 0° C., to a stirred solution of the 1.95 g of H-Leu-Lys(Z)-Phe-OtBu obtained above, 2.2 g of Fmoc-Lys(Z)-Phe-OH and 533 mg of HOObt in 20 ml of dimethylformamide. The mixture is left to stand as usual, the precipitate is filtered off with suction, and the filtrate is concentrated. The residue is triturated with saturated NaHCO$_3$ solution and filtered off with suction.

Yield 3.14 g, melting point 178°–182° C., $[\alpha]_D^{22} = -20.8°$ (c=1 in 90% strength acetic acid). J (d) H-Lys-Phe-Leu-Lys-Phe-OtBu triacetate 1 g of Fmoc-Lys(Z)-Phe-Leu-Lys(Z)-Phe-OtBu is catalytically hydrogenated in analogy to Example 1b.

Yield 750 mg.

The substance obtained above is purified by chromatography in analogy to Example 25d.

Yield 450 mg, $[\alpha]_D^{23} = -25.5°$ (c=1 in water).

(e) H-Lys-Phe-Leu-Lys-Phe-OH diacetate 2.1 g of Fmoc-Lys(Z)-Phe-Leu-Lys(Z)-Phe-OtBu are dissolved in 21 ml of 90% strength aqueous trifluoroacetic acid. The solution is left to stand at room temperature for 1 hour, and concentrated in vacuo. The residue is triturated with diethyl ether and filtered off with suction.

Yield 1.99 g.

1 g of the Fmoc-Lys(Z)-Phe-Leu-Lys(Z)-Phe-OH obtained above is catalytically hydrogenated in analogy to Example 1b.

Yield 630 mg.

For purification, the 630 mg obtained above are purified by chromatography in analogy to Example 25d.

Yield 458 mg, $[\alpha]_D^{23} = -9 7°$ (c=1 in water).

EXAMPLE 28

H-Lys-Phe-Leu-Lys-Phe-NH$_2$ triacetate 182 mg of DCC are added, at 0° C., to a stirred solution of 970 mg (0.83 mmol) of Fmoc-Lys(Z)-Phe-Leu-Lys(Z)-Phej 30 OH (see Example 27e) and 126 mg of HOBt.NH$_3$ in 10 ml of dimethylformamide. The working-up is carried out in analogy to Example 27c (last paragraph).

Yield 950 mg.

The 950 mg of Fmoc-Lys(Z)-Phe-Leu-Lys(Z)-Phe-NH$_2$ obtained above are catalytically hydrogenated in analogy to Example 1b.

Yield 635 mg.

The 635 mg of H-Lys-Phe-Leu-Lys-Phe-NH$_2$ triacetate obtained above are purified by chromatography in analogy to Example 25d.

Yield 298 mg, $[\alpha]_D^{23} = -21.4°$ (c=1 in water).

EXAMPLE 29

H-Arg-Ile-Val-Arg-Ile-OH (a) Fmoc-Val-Arg-OH 14.55 g of Fmoc-Val-OObt are added, at room temperature, to a stirred suspension of 5.23 g (30 mmol) of arginine, 4.89 g of HOObt and 5.4 g of pyridinium perchlorate. The mixture is left to stir until everything has dissolved, and is left to stand overnight. The solution is concentrated, and water is added to the residue. The pH is adjusted to 7 with NaHCO$_3$ solution. The precipitate which forms is filtered off with suction and washed with water.

Yield 470 mg, $[\alpha]_D^{21} = -16.6°$ (c=1 in methanol).

(b) Fmoc-Val-Arg-Ile-OBzl 660 mg of DCC are added, at 0° C., to a stirred solution of 1.49 g (3 mmol) of Fmoc-Val-Arg-OH, 1.18 g of H-IleOBzl tosylate and 489 mg of HOObt in 15 ml of dimethylformamide. The working-up is carried out in analogy to Example 2b.

Yield 2.2 g, $[\alpha]_D^{21} = -30.0°$ (c=1 in methanol).

(c) Fmoc-Arg-Ile-OtBu 2.2 g of DCC are added, at 0° C., to a stirred solution of 2.23 g of H-Ile-OtBu.HCl, 4 g (10 mmol) of Fmoc-Arg-OH and 1.35 g of HOBt in 80 ml of dimethylformamide. The working-up is carried out in analogy to Example 2b.

Yield 5.65 g, $[\alpha]_D^{21} = -13.8°$ (c=1 in methanol).

(d) Fmoc-Arg-Ile-OH 15.8 g of Fmoc-Arg-Ile-OtBu are dissolved in 150 ml of 90% strength aqueous trifluoroacetic acid. The solution is left to stand at room temperature for 1 hour, and is concentrated. The residue is triturated twice with diethyl ether, the ether being decanted off each time. Water is added to the residue, and the pH is adjusted to with saturated NaHCO$_3$ solution. The precipitate is filtered off with suction and dried.

Yield 9.8 g, $[\alpha]_D^{21} = -5.3°$ (c=1 in methanol).

(e) H-Val-Arg-Ile-OBzl 31.5 ml of diethylamine are added to a solution of 21 g (30 mmol) of Fmoc-Val-Arg-Ile-OBzl in 200 ml of dimethylformamide. The mixture is left to stand at room temperature for 10 minutes, and is concentrated in vacuo. The residue is triturated with diethyl ether and filtered off with suction.

Yield 13.85 g, $[\alpha]_D^{21} = -27.21°$ (c=1 in methanol).

(f) Fmoc-Arg-Ile-Val-Arg-Ile-OBzl 3.3 g of DCC are added, at 0° C., to a stirred solution of 7.4 g (15 mmol) of Fmoc-Arg-Ile-OH, 7.15 g of H-Val-Arg-Ile-OBzl and 2.44 g of HOObt in 150 ml of dimethylformamide. The working-up is carried out in analogy to Example 2b. The dried residue is triturated with ethyl acetate, filtered off with suction and dried.

Yield 14.1 g, $[\alpha]_D^{21} = -33.5°$ (c=1 in methanol).

(g) H-Arg-Ile-Val-Arg-Ile-OBzl triacetate 3.15 ml of diethylamine are added to a solution of 2.9 g (3 mmol) of Fmoc-Arg-Ile-Val-Arg-Ile-OBzl in 20 ml of dimethylformamide, and the mixture is left to stand at room temperature for 10 minutes. It is then concentrated in vacuo, and the residue is triturated with diethyl ether.

Yield 2.7 g.

800 mg of the substance obtained above are purified by chromatography in analogy to Example 25d.

Yield 725 mg, $[\alpha]_D^{24} = -27.7°$ (c=1 in 90% strength acetic acid).

(h) H-Arg-Ile-Val-Arg-Ile-OH diacetate 1.5 g of H-Arg-Ile-Val-Arg-Ile-OBzl (crude substance) are catalytically hydrogenated in analogy to Example 1b.

Yield 1.3 g.

700 mg of the substance obtained above are purified by chromatography in analogy to Example 25d.

Yield 405 mg, $[\alpha]_D^{22} = -47.1°$ (c=1 in water).

EXAMPLE 30

Cyclo(D-Arg-Ile-D-Leu-Arg-Ile) diacetate 1.4 g of H-D-Arg-Ile-D-Leu-Arg-Ile-OH diacetate (see Example 13c) are chromatographed on a weakly basic ion exchanger in the perchlorate form. The eluate is freezedried.

Yield 1.343 g of H-D-Arg-Ile-D-Leu-Arg-Ile-OH diperchlorate.

A solution of 670 mg (1 mmol) of the H-D-Arg-Ile-D-Leu-Arg-Ile-OH diperchlorate obtained above, 270 mg of HOBt and 0.13 ml of N-ethylmorpholine in 100 ml of dimethylformamide is slowly added dropwise, at room temperature, to a stirred solution of 440 mg of DCC in 50 ml of dimethylformamide. The mixture is left to stand at room temperature overnight. The next day, a further 300 mg of DCC are added, and the mixture is left to stand at room temperature for 2 days. It is then concentrated in vacuo. The residue is partitioned between ethyl acetate and dilute aqueous acetic acid. The aqueous phase is freeze-dried.

Yield 665 mg.

The substance obtained above is chromatographed on a weakly basic ion exchanger in the acetate form. Water is used as the eluting agent. The combined peptide-containing eluate is freeze-dried.

Yield 548 mg, $[\alpha]_D^{23} = -16.7°$ (c=1 in water).

EXAMPLE 31

H-Arg-Pro-Cys(StBu)-Arg-Phe-OtBu (a) Fmoc-Arg-Pro-OtBu.HClO$_4$ 3.3 g of DCC are added, at 0° C., to a stirred solution of 5.95 g (15 mmol) of Fmoc-Arg-OH, 2.57 g of H-Pro-OtBu, 2.02 g of HOBt and 2.7 g of pyridinium perchlorate in 0 ml of dimethylformamide. The working-up is carried out in analogy to Example 1a. The residue is triturated with diethyl ether and filtered off with suction.

Yield 9.4 g

For characterization, 750 mg of the substance obtained above are dissolved in 40% strength aqueous acetic acid, and the solution is chromatographed on a weakly basic ion exchanger in the acetate form. The eluate is concentrated and freeze-dried.

Yield 690 mg of Fmoc-Arg-Pro-OtBu acetate, $C_{32}H_{43}N_5O_7$, (MW 609.7), $[\alpha]_D^{20} = -44.2°$ (c=1 in methanol), purity of substance according to amino acid analysis: 93%

(b) Fmoc-Arg-Pro-OH 8.5 g of Fmoc-Arg-Pro-OtBu.HClO$_4$ are dissolved in 85 ml of 90% strength aqueous trifluoroacetic acid. The solution is left to stand at room temperature for 1 hour, and is concentrated in vacuo. The residue is triturated with diethyl ether and filtered off with suction.

Yield 7.9 g.

7.16 g of the substance obtained above are suspended in 100 ml of water. The pH is adjusted to 6 with saturated NaHCO₃ solution. The mixture is left to stand at 40C for 2 days, and the precipitate is filtered off with suction
and dried over P₂O₅ in vacuo.

Yield 6.15 g, $[\alpha]_D^{20} = -32.2°$ (c=1 in 80% strength aqueous acetic acid).

(c) Z-Arg(Z₂)-Phe-OtBu 6.6 g of DCC are added, at 0° C., to a stirred solution of 17.3 g (30 mmol) of Z-Arg(Z₂)—OH, 7.73 g of H-Phe-OtBu.HCl, 4.9 g of HOObt and 3.9 ml of N-ethylmorpholine in 70 ml of dimethylformamide. The working-up is carried out in analogy to Example 1a. The residue is triturated 5 with diethyl ether, filtered off with suction and dried in vacuo.

Yield 19 g, $[\alpha]_D^{20} = -0.5°$ (c=1 in 80% strength aqueous acetic acid).

(d) H-Arg-Phe-OtBu.HClO₄

18.6 g of Z-Arg(Z₂)-Phe-OtBu are dissolved in 200 ml of dimethylacetamide and catalytically hydrogenated on Pd/C with hydrogen. A pH of 5 is maintained during the hydrogenation by addition of 1N HClO₄ using an autotitrator. After the hydrogenation is complete, the catalyst is filtered off with suction, and the filtrate is concentrated. The residue is dissolved in water, and the solution is filtered through a clarifying layer and freezedried.

Yield 21.1 g of oil.

The oil is triturated twice with diethyl ether, the diethyl ether is decanted off, and the oily residue is dried in vacuo.

Yield 18.5 g (135%, and thus still contains solvent).

(e) Fmoc-Cys(StBu)-Arg-Phe-OtBu acetate 2.2 g of DCC are added, at 0° C., to a stirred solution of 4.31 g (10 mmol) of Fmoc-Cys(StBu)—OH, 7.74 g of H-Arg-Phe-OtBu.2 HClO₄ (oily substance obtained above), 1.35 g of HOBt and 1.3 ml of N-ethylmorpholine in 40 ml of dimethylformamide. The mixture is worked up in analogy to Example 1a. The residue is triturated with diethyl ether and dried.

Yield 8 g.

1.3 g of the substance obtained above are dissolved in 30 ml of 55% strength acetic acid, and the solution is chromatographed on a weakly basic ion exchanger in the acetate form. 55% strength acetic acid is used for elution. The eluate is concentrated, and the residue is taken up in water and freeze-dried.

Yield 1.06 g, $[\alpha]_D^{29} = -45.5°$ (c=1 in methanol), content of peptide base according to amino acid analysis: 79%.

(f) H-Cys(StBu)-Arg-Phe-OtBu.HClO₄

21 ml (200 mmol) of diethylamine are added, at room temperature, to a solution of 17.84 g (20 mmol) of Fmoc-Cys-(StBu)-Arg-Phe-OtBu.HClO₄ (crude substance from Example e) in 100 ml of dimethylformamide. The mixture is stirred at room temperature for 10 minutes, and is concentrated in vacuo. The residue is triturated twice with diethyl ether, with decantation. The oily residue is dried under high vacuum.

Yield 14.6 g.

(g) Fmoc-Arg-Pro-Cys(StBu)-Arg-Phe-OtBu diacetate 2.2 g of DCC are added, at 0° C., to a solution of 4.94 g (10 mmol) Fmoc-Arg-Pro-OH, 5.7 g (10 mmol) of H-Cys(StBu)-Arg-Phe-OtBu.HClO₄, 163 mg of HOObt and 1.8 g of pyridinium perchlorate in 100 ml of dimethylformamide. The working-up is carried out in analogy to Example 1a. The residue is triturated with diethyl ether.

Yield 8.7 g.

500 mg of the substance obtained above are purified by chromatography in analogy to Example 25d.

Yield 341 mg, $[\alpha]_D^{22} = -60.8°$ (c=1, water), content of peptide base according to amino acid analysis: 77%.

(h) H-Arg-Pro-Cys(StBu)-Arg-Phe-OtBu triacetate 3.32 ml of diethylamine are added to a solution of 3.3 g of Fmoc-Arg-Pro-Cys(StBu)-Arg-Phe-OtBu (crude substance) in 20 ml of dimethylformamide. After 10 minutes at room temperature, the mixture is concentrated in vacuo. The residue is triturated with ether and filtered off with suction.

Yield 2.7 g.

The substance is purified by chromatography in analogy to

EXAMPLE 25d.

Yield 1.23 g, $[\alpha]_D^{22} = -42.4°$ (c=1 in water), content of peptide base according to amino acid analysis: 72%.

EXAMPLE 32

Cyclo(D-Arg-Ile-D-Leu-Arg-0=Val)

(a) Fmoc-D-Leu-Arg-OH 9.97 g of Fmoc-D-Leu-OObt are added, at room temperature, to a stirred suspension of 3.48 g (20 mmol) of arginine, 3.26 g of HOObt and 3.6 g of pyridinium perchlorate in 100 ml of dimethylformamide. The mixture is stirred until everything has dissolved, and is left to stand overnight. It is then concentrated, and water is added to the residue. The pH is adjusted to 7 by addition of NaHCO₃ solution. The precipitate is filtered off with suction and dried.

Yield 10.2 g, $[\alpha]_D^{20} = +29.2$ (c=1 in methanol).

(b) Fmoc-D-Leu-Arg-D-Val-OBzl 3.3 g of DCC are added, at 0° C., to a stirred solution of 7.64 g (15 mmol) of Fmoc-D-Leu-Arg-OH, 5.7 g of H-D-Val-OBzl tosylate and 2.45 g of HOObt in 75 ml of dimethylformamide. The process is carried out as usual, and the residue is partitioned between ethyl acetate and saturated NaHCO₃ solution. The ethyl acetate solution is then extracted by shaking with water, dried over Na₂SO₄ and concentrated.

Yield 8.2 g, $[\alpha]_D^{20} = +11.2°$ (c=1 in methanol).

(c) H-D-Leu-Arg-D-Val-OBzl 12.05 ml of diethylamine are added to a solution of 8.04 g (11.5 mmol) of Fmoc-D-Leu-Arg-D-Val-OBzl in 60 ml of dimethylformamide. The mixture is left to stand at room temperature for 15 minutes, and is concentrated. The residue is partitioned between n-pentanol and NaHCO₃ solution. The pentanol phase is concentrated, and the residue is triturated with diethyl ether.

Yield 3.8 g, $[\alpha]_D^{20} = -3.0°$ (c=1 in methanol).

(d) Z-D-Arg-Ile-D-Leu-Arg-D-Val-OBzl diacetate 1.65 g of DCC are added, at 0° C., to a stirred solution of 3.16 g of Z-D-Arg-Ile-OH (see Example 9b), 3.57 g of H-D-Leu-Arg-D-Val-OBzl, 1.23 g of HOObt and 1.35 g of pyridinium perchlorate in 75 ml of dimethylformamide. The working-up is carried out as usual, and the residue is partitioned between n-pentanol and half-saturated NaHCO₃ solution. The n-pentanol phase is concentrated, and the residue is triturated with ethyl acetate and filtered off with suction. The substance is subjected to countercurrent partition between ethyl acetate and 10% strength aqueous acetic acid in 5 stages. The compound is in the acetic acid phases. They are combined and concentrated. The residue is triturated with diethyl ether.

Yield 4.55 g $[\alpha]_D^{25} = +11.4°$ (c=1 in methanol).

(e) H-D-Arg-Ile-D-Leu-Arg-D-Val-OH diacetate 4.4 g of Z-D-Arg-Ile-D-Leu-Arg-D-Val-OBzl are catalytically hydrogenated in analogy to Example 1b.

Yield 3.7 g.

700 mg of the compound obtained above are purified by chromatography in analogy to Example 25d.

Yield 350 mg, $[\alpha]_D^{22} = -10.6°$ (c=1 in water).

(f) Cyclo(D-Arg-Ile-D-Leu-Arg-D-Val) diacetate 2 g of H-D-Arg-Ile-D-Leu-Arg-D-Val-OH diacetate (crude substance) are converted into the corresponding diperchlorate in analogy to Example 30.

Yield 1.78 g.

656 mg (1 mmol) of the substance obtained above are cyclized in analogy to Example 30.

Yield 683 mg.

The substance obtained above is purified by chromatography in analogy to Example 25d.

Yield 366 mg, $[\alpha]_D^{21} = +20.5°$ (c=1 in water).

Abbreviations used:

The abbreviations used for amino acids correspond to the three-letter code customary in peptide chemistry as described in, for example, Europ. J. Biochem. 138, 9 (1984). Some other abbreviations are listed below:

| | |
|---|---|
| Boc | tert.-butyloxycarbonyl |
| Bzl | benzyl |
| Fmoc | 9-fluorenylmethyloxycarbonyl |
| Me | methyl |
| Ac | acetyl |
| DCC | dicyclohexylcarbodiimide |
| FAB | fast atom bombardment |
| HOBt | 1-hydroxybenzotriazole |
| M | molecular peak |
| Z | benzyloxycarbonyl |
| NSu | succinimido |
| Tcp | 2,4,5-trichlorophenyl |
| HOObt | 3-hydroxy-4-oxo-3,4-dihydro-benzo[d]-1,2,3-triazine |
| DCHA | dicyclohexylamine |

We claim:

1. A compound of formula I

in which $R^N$ represents a radical of the formula II;

$R^2$ represents hydrogen or a radical of the formula $R-[A]_n-NH-$;

$R^3$ denotes amino, guanidino, ($C_1-C_3$)-alkylamino or di-($C_1-C_3$)-alkylamino;

m denotes an integer from 1 to 6;

A represents a radical of the formula $-NH-CR^4R^5-CO-$;

R denotes hydrogen, ($C_1-C_6$)-alkanoyl, ($C_7-C_{11}$)-aroyl, in which the aromatic moiety is unsubstituted or mono- or disubstituted by ($C_1-C_4$)-alkyl, ($C_1-C_4$)-alkoxy, ($C_1-C_4$)-alkylthio, halogen, carbamoyl, ($C_1-C_4$)-alkoxycarbonyl and/or sulfamoyl, or is monosubstituted by methylenedioxy, or denotes ($C_5-C_7$)-cycloalkyl-($C_1-C_3$)-alkanoyl or ($C_6-C_{14}$)-aryl-($C_1-C_3$)-alkanoyl, where a $-CH_2$ group in the radicals where R is not a hydrogen can be replaced by $-O-$ or $-S-$;

n is 0 or, if p=1, n represents 1;

$R^4$ and $R^5$ are identical or different and denote hydrogen, ($C_1-C_6$)-alkyl or ($C_7-C_{11}$)-aralkanoyl;

L represents Pro, D-Pro or a radical of the formula $-NH-CH(R^6)-CO-$;

$R^6$ denotes ($C_1-C_6$)-alkyl which is unsubstituted or monosubstituted by hydroxyl, ($C_1-C_6$)-alkoxy, ($C_1-C_6$)-alkoxy-carbonyl, carbamoyl or R-NH, R being as defined above but cannot be hydrogen, or denotes ($C_7-C_{11}$)-aralkyl which is unsubstituted or monosubstituted on the aromatic ring by ($C_1-C_6$)-alkoxy, or denotes 3-indolylmethyl;

N represents Pro, D-Pro or a radical of the formula $-NH-CH(R^7)-CO-$;

$R^7$ denotes ($C_1-C_6$)-alkyl which is unsubstituted or monosubstituted by hydroxyl, ($C_1-C_6$)-alkoxy, ($C_1-C_6$)-alkoxycarbonyl, carbamoyl or R-NH, R being as defined above but cannot be hydrogen, or denotes ($C_7-C_{11}$)-aralkyl which is unsubstituted or monosubstituted on the aromatic ring by ($C_1-C_6$)-alkoxy, or denotes 3-indolylmethyl;

$B^2$ represents Arg, D-Arg, Lys or D-Lys;

$R^C$ represents a radical of the formula $-NR^9-CH(R^8)-(CO)_p-R^1$;

$R^8$ is defined as $R^7$, with CH, $CH_2$ or $CH_3$ radicals which are present in the $\beta$-position with respect to $-NH-$ optionally being monohydroxylated, and $R^9$ denotes hydrogen; or $R^8$ and $R^9$ together denote $-[CH_2]_3-$ or $[CH_2]_4$;

p is 0 or 1

$R^1$ represents hydrogen, hydroxyl or ($C_1-C_6$)-alkoxy in the case of p=0;

$R^1$ represents $OR^{10}$ or $NR^{10}R^{11}$ in the case of p=1; and $R^{10}$ and $R^{11}$ are identical or different and denote hydrogen, ($C_1-C_6$)-alkyl or ($C_7-C_{11}$)-aralkyl; or $NR^{10}R^{11}$ represents pyrrolidino, piperidino or morpholino; or p is 1, or if n=0, p represents 0;

R and $R^1$ together denote a bond, and the other radicals are as defined above, and its physiologically tolerated salts.

2. A compound of the formula I as claimed in claim 1, in which

L represents the radical of isoleucine, valine, threonine, serine, O-($C_1-C_9$)-alkylthreonine, O-($C_1-C_9$)-alkylserine, leucine, proline or of the $\omega$-($C_1-C_6$)-alkyl ester, preferably tert.butyl ester, of glutamic acid or aspartic acid;

N represents the radical of valine, isoleucine, leucine, phenylalanine, tryptophan, tyrosine which is optionally O-($C_1-C_6$)-alkylated, glutamine, asparagine, $\gamma$-($C_1-C_6$)-alkyl glutamate or $\beta$-($C_1-C_6$)-alkyl aspartate or $\epsilon$-acyl-lysine, and $B^2$ denotes Arg, D-Arg, Lys or D-Lys, and its physiologically tolerated salts.

3. A compound of the formula I as claimed in claim 1, in which p is 1 and R and $R^1$ together represent a bond, and its physiologically tolerated salts.

4. A compound of the formula I as claimed in claim 1, in which R and R¹ do not together represent a bond, and its physiologically tolerated salts.

5. A method for the treatment of disturbances of diuresis, which comprises administration of an effective amount of a compound of the formula I as claimed in claim 1, or of its physiologically tolerated salt.

6. A method for the treatment of hypertension and dropsy, which comprises administration of an effective amount of a compound of the formula I as claimed in claim 1, or of its physiologically tolerated salt.

7. A method for the treatment of polyuria or diabetes insipidus, which comprises administration of an effective amount of a compound of the formula I as claimed in claim 1, or of its physiologically tolerated salt.

8. A pharmaceutical formulation for the treatment of disturbances of diuresis, hypertension and dropsy, polyuria or diabetes insipidus comprising an effective amount of the compound of the formula I as claimed in claim 1, or of its physiologically tolerated salt, and a pharmaceutically acceptable vehicle.

9. A compound according to the formula cyclo-(Gly-Arg-Ile-Phe-Arg-Ile).

10. A compound according to the formula cyclo-(Gly-Arg-Ile-Leu-Arg-Ile).

11. A compound according to the formula cyclo-(D-Arg-Ile-D-Leu-Arg-Ile).

12. A compound according to the formula cyclo-(D-Arg-Ile-D-Leu-Arg-Ile) diacetate.

13. A compound according to the formula cyclo-(D-Arg-Ile-D-Leu-Arg-D-Val).

* * * * *